United States Patent [19]

Fujii et al.

[11] Patent Number: 4,566,330

[45] Date of Patent: Jan. 28, 1986

[54] ULTRASONIC MEASUREMENT METHOD, AND APPARATUS THEREFOR

[75] Inventors: Tadashi Fujii, Fujinomiya; Yoshinori Hayakawa, Ibaraki, both of Japan

[73] Assignee: Terumo Kabushiki Kaisha, Tokyo, Japan

[21] Appl. No.: 657,028

[22] Filed: Oct. 2, 1984

[30] Foreign Application Priority Data

Dec. 7, 1983 [JP] Japan .................... 58-229853

[51] Int. Cl.⁴ .................................. G01N 29/00
[52] U.S. Cl. ........................... 73/599; 73/602; 73/1 DV
[58] Field of Search ............ 73/599, 1 DV, 600, 602, 73/606, 607, 620, 629; 128/660

[56] References Cited

U.S. PATENT DOCUMENTS 4,414,850 11/1983 Miwa et al. ..................... 73/599
4,509,524 4/1985 Miwa ............................ 73/599

FOREIGN PATENT DOCUMENTS 56-147082 11/1981 Japan .

Primary Examiner—Stephen A. Kreitman
Attorney, Agent, or Firm—Frishauf, Holtz, Goodman & Woodward

[57] ABSTRACT

A method and apparatus for ultrasonic measurement in which ultrasonic pulses having a plurality of different frequencies are transmitted into in order to object under investigation and derive a mean value of attenuation coefficients indicative of attenuation within the object, as well as the frequency dependence of the attenuation coefficient. If the frequency dependence of the reflection intensity from the object under investigation is constant or proportional to frequency within a range of measured frequencies, it is possible to obtain the attenuation coefficient and the coefficient indicative of its frequency dependence within a small area of the object by measuring the echo intensity of emitted ultrasonic pulses having three different frequencies. Furthermore, extending the above-mentioned processing over all small areas of the entire object enables obtaining a two-dimensional distribution image indicative of the attenuation coefficient and its frequency dependence.

10 Claims, 18 Drawing Figures

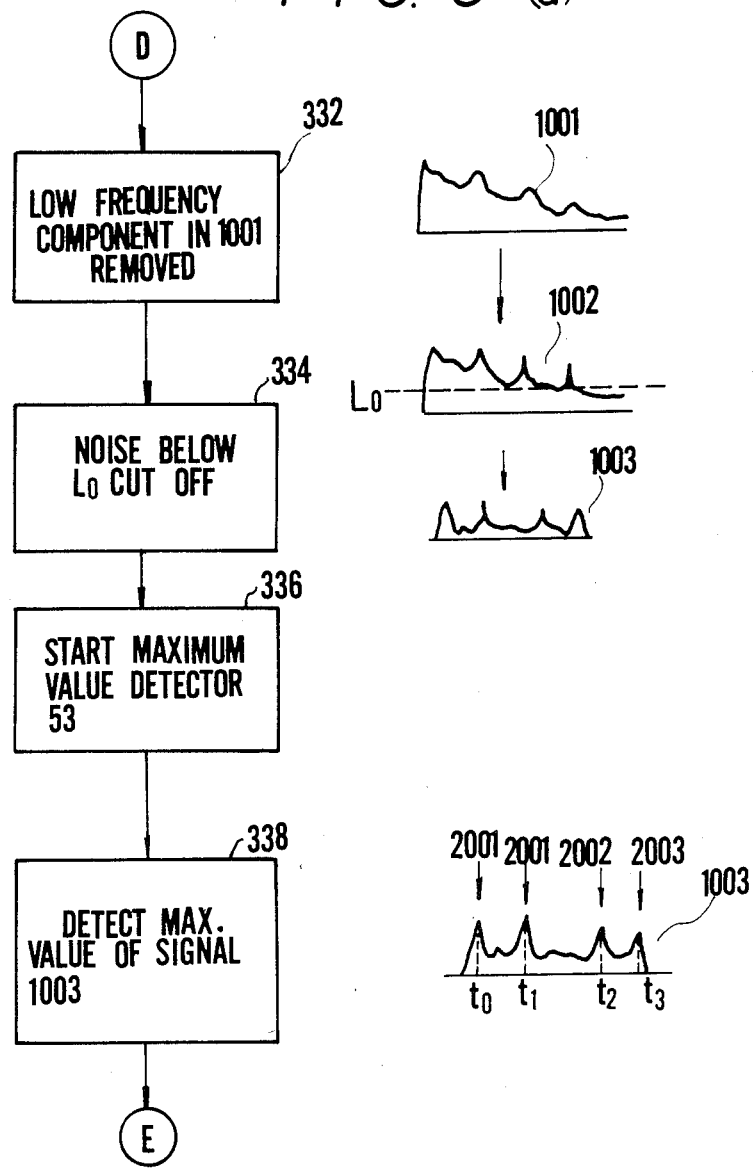

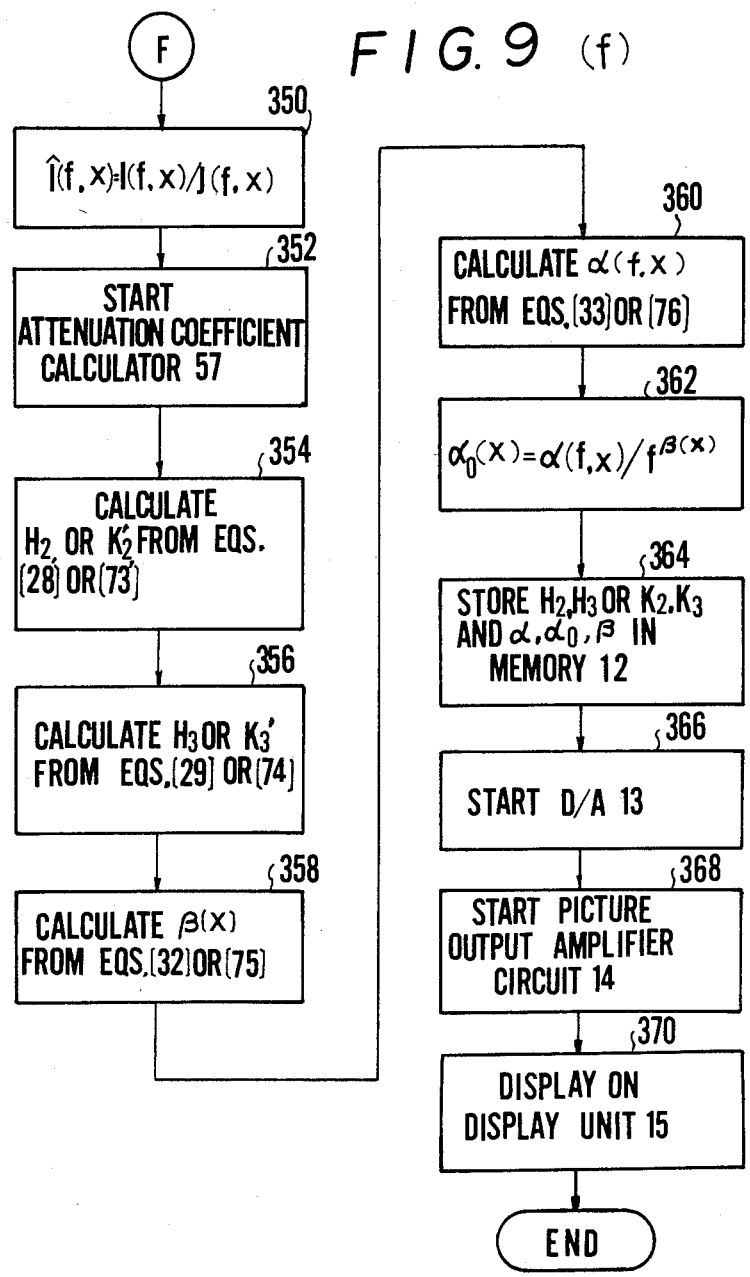

ULTRASONIC MEASUREMENT METHOD, AND APPARATUS THEREFOR

BACKGROUND OF THE INVENTION

This invention relates to improvements in an ultrasonic measurement method for subjecting an object to an ultrasonic transmission and receiving reflected ultrasonic waves from the interior of the object to measure the acoustic characteristics of the object. More particularly, the invention relates to an ultrasonic measurement method and apparatus for providing information relating to attenuation that accompanies propagation of ultrasonic waves in the interior of an object.

Ultrasonic measurement techniques find application widely in such fields as material testing, SONAR and medical diagnosis. In particular, ultrasound scanner systems for medical purposes have recently been developed.

The principle of operation of an ultrasound scanner apparatus resides in use of a pulse-echo method and utilizes a phenomenon wherein an ultrasonic pulse transmitted into a living body, which is the object undergoing measurement, is reflected at a boundary where there is a difference in acoustic impedence.

The reflected wave (echo) is received and processed to display a tomograph of the living body by a so-called B-mode method. The echo contains a variety of information such as the ultrasonic attenuation, acoustic impedance and propagation velocity of sound. With an apparatus of this kind, however, these various items of information cannot be separated from one another distinctly, so that the general practice is merely to display the amplitude of the echo.

More specifically, the propagation velocity of sound is assumed to be constant and, with regard to attenuation ascribable to ultrasonic propagation, the value of echo amplitude arbitrarily corrected by a so-called STC (sensitivity time control) circuit is luminance-modulated, with the modulated amplitude being displayed on a cathode-ray tube as a tomograph. Accordingly, the tomograph obtained is a two-dimensional distribution at the acoustic impedance interface rendered qualitatively into a picture, so that the morphological information relating to the position and shape of the bioligical tissue inevitably forms the core of the information utilized. In other words, the state of the art is such that such biological tissue characteristics as degree of attenuation and propagation velocity of sound are not measured.

Several attempts at attaining attenuation information relating to biological tissue have been reported. As will be described below in further detail, an echo signal contains two types of information, namely attenuation due to propagation through biological tissue, and intensity of reflection at an interface or boundary where there is a difference in acoustic impedence. Both of these quantities are unknown. Therefore, isolating the affects of these two quantities is extremely difficult at the present time.

If the reflected intensity is assumed to be independent of the frequency of the ultrasonic waves and ultrasonic waves having a plurality of different frequencies are transmitted and received with regard to the same portion of the object under measurement followed by measuring the sound pressure ratio of each frequency component of the echo, then it will be possible to eliminate the influence of the reflected intensity and derive an attenuation coefficient ascribable to propagation without the affects of the reflected intensity. The foregoing assumption holds in the case of an acoustic boundary having a sufficiently wide range in comparison with the wavelength of the ultrasonic waves, e.g. in the case of a planar reflector. In actuality, however, a scatterer having a size approximately equivalent to or less than the wavelengths used can reside at the biological tissue. It is therefore difficult to consider that the foregoing assumption will always hold for an entire bioligical tissue.

In view of the foregoing circumstances, the applicant has proposed, in Japanese Patent Application Laid-Open No.56-147082, a method and apparatus for measuring attenuation information ascribable to ultrasonic propagation in a living body in which the influence of reflected intensity at an acoustic boundary is reduced. However, the ultrasonic attenuation information obtained according to the invention of this earlier application is not an attenuation coefficient but an equation of the first degree involving a mean value of ultrasonic attenuation coefficients over a prescribed interval.

SUMMARY OF THE INVENTION

An object of the present invention is to provide an ultrasonic measurement method and apparatus for measuring by approximation the attenuation coefficient of an object as well as the frequency dependence of the attenuation coefficient.

According to the present invention, the foregoing object is attained by providing an ultrasonic measurement method for transmitting ultrasonic pulses having a plurality of different frequencies into an object under investigation, detecting echos of the ultrasonic pulses reflected from within the object, and subjecting the detected echos, which will exhibit a plurality of frequencies, to information processing to obtain quantitative information relating to the ultrasonic characteristics of the object. A characterizing feature of the inventive method is the derivation of information relating to the attenuation coefficient of the object from the mean value of attenuation coefficients measured on the basis of two different frequencies, and either the mean value of attenuation coefficients or a mean value of a function of attenuation coefficient and frequencies measured on the basis of three different frequencies inclusive of the first two frequencies.

According to a characterizing feature of the present invention, the information relating to the attenuation coefficient includes an attenuation coefficient of ultrasonic waves in the object.

According to another characterizing feature of the present invention, the information relating to the attenuation coefficient includes the frequency dependence of the attenuation coefficient of ultrasonic waves in the object.

The present invention further provides an apparatus for practicing the foregoing ultrasonic measurement method. The apparatus includes means for transmitting ultrasonic pulses having a plurality of different frequencies into an object under investigation, means for detecting echos of the ultrasonic pulses reflected from within the object, means for displaying quantitative information obtained, and means for subjecting the detected echos, which will exhibit a plurality of frequencies, to information processing to obtain quantitative information relating to the ultrasonic characteristics of the object.

This last-mentioned means obtains the mean value of attenuation coefficients having two different frequencies, and either the mean value of attenuation coefficients having three different frequencies inclusive of the first two frequencies or the mean value of the function of attenuation coefficient and frequencies which are said-three different frequencies inclusive of the first two frequencies, and derives information relating to the attenuation coefficient of the object on the basis of the mean values obtained.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

An embodiment of an ultrasonic measurement method according to the present invention will now be described in detail with reference to the accompanying drawings.

Figure 1:
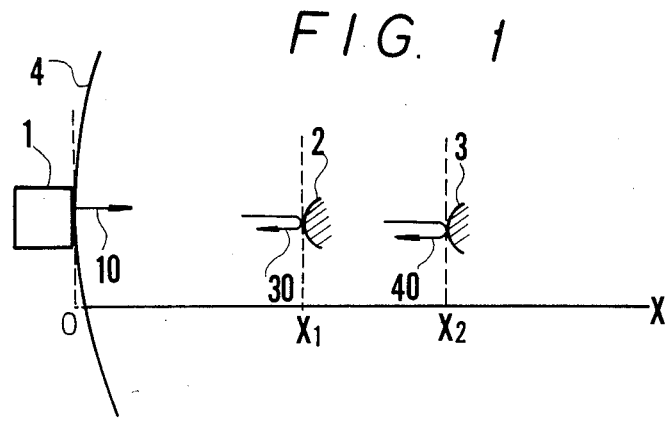
FIGS. 1 and 2 are views useful in describing the fundamental principle of the present invention.
Figure 2:
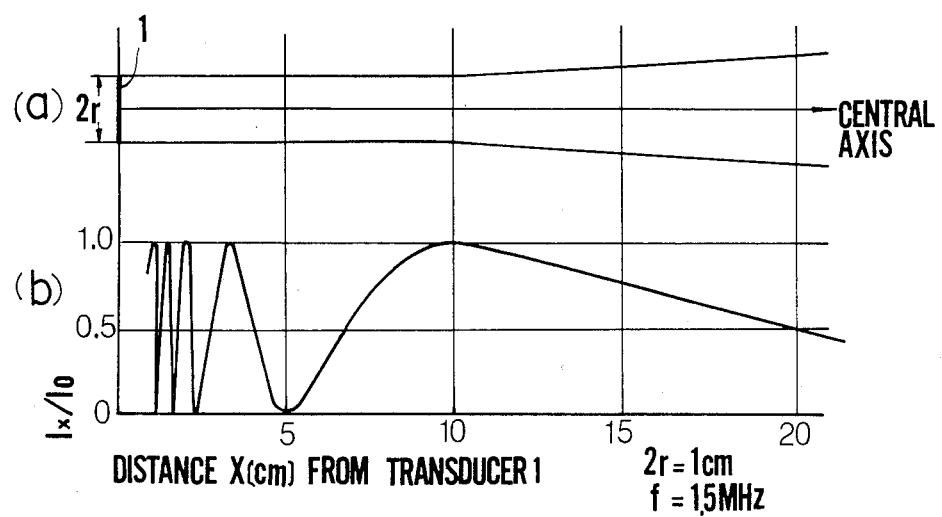
Figure 3:
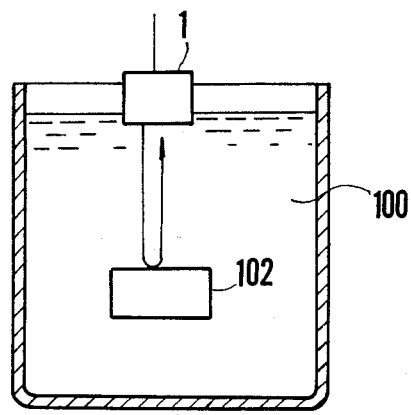
FIGS. 3, 4 and 5 are views useful in describing the calibration of an ultrasound field of an ultrasonic probe used in an embodiment of the present invention.
Figure 4:
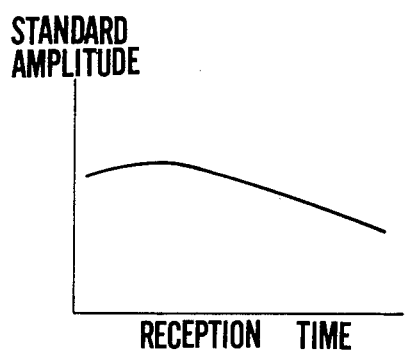

The principle of the present invention will be described in conjunction with FIG. 1. An ultrasonic pulse 10 transmitted into an object 4 by an ultrasonic probe 1 is reflected at each of two surfaces 2, 3 where acoustic characteristics are discontinuous, resulting in reflected pulses 30, 40, respectively, which are detected by the probe 1. If we let t represent the elapsed time from emission of the ultrasonic pulse to reception of the reflected pulse, the distance x from the ultrasonic probe 1 to a surface of ultrasonic characteristic discontinuity will be given by the following equation, where V is the prpagation velocity of sound:

$$x = V \cdot t / 2$$

If we let $I_0(f)$ represent the intensity of the pulse 10 emitted at a frequency f, and let I(f, x) represent the intensity of a received reflected pulse, the following equation, indicative of an approximation, will hold:

$$I(f,x) = I_0(f) f^{a(f,x)} g(x) x^{b(x)} \exp\left(-4 \int_0^x \alpha(f,x) dx\right) \quad (1)$$

Taking the natural logarithm of both sides of Eq. (1) will result in the following:

$$\ln I(f,x) = \ln I_0(f) + a(f,x)\ln f + \ln(g(x)x^{b(x)}) - 4 \int_0^x \alpha(f,x) dx \quad (2)$$

Here, $\alpha(f,x)$ is the attenuation coefficient ascribable to ultrasonic propagation within the object 4. In Eq. (1), $f^{a(f,x)} \cdot g(x)$ is the reflection intensity of the acoustic characteristic discontinuity surface with frequency dependence being taken into consideration.

With regard to the value of a(f,x), $a(f,x) = 0$ will hold at an acoustic characteristic discontinuity surface sufficiently larger than the wavelength ($\lambda = V/f$), whereas $a(f,x) = 4$ will hold an acoustic characteristic discontinuity surface sufficiently smaller than the wavelength. Within a certain frequency range, therefore, a(f,x) will be constant, and the relation $0 \leq a(f,x) \leq 4$ may be considered to hold for a living body. Further, $x^{b(x)}$ may be considered as being the effect of a weakening in the reflection intensity at the position of the ultrasonic probe owing to spread of the reflected wave. At a sufficiently broad acoustic characteristic discontinuity surface, $b(x) = 0$ will hold, whereas $b(x) = -2$ will prevail at a small acoustic characteristic continuity surface. In general, therefore, the relation $-2 \leq b(x) \leq 0$ will hold.

In the foregoing considerations, the emitted ultrasonic wave 10 ideally is a fine pencil beam, and the effects of mutual interference among the waves reflected at a plurality of acoustic characteristic discontinuity surfaces located close to one another is neglected.

The principal of carrying out information processing based on the echo intensity distribution to obtain quantitative information relating to the ultrasonic characteristics of the object 4 starts with Eq. (2).

To facilitate the mathematical perspective, we will subject both sides of Eq. (2) to a first order partial differentiation with respect to x, assuming that the echo intensity I(f,x) is obtained continuously, with regard to the distance x and frequency f. This will result in the following:

$$\frac{\partial}{\partial x}[\ln I(f,x)] = \ln f \cdot \frac{\partial}{\partial x}[a(f,x)] + \frac{\partial}{\partial x}[\ln(g(x) \cdot x^{b(x)})] - 4\alpha(f,x) \quad (3)$$

Peforming a first order partial differentiation with respect to the frequency f gives us:

$$\frac{\partial^2}{\partial f \partial x}[\ln I(f,x)] = \ln f \cdot \frac{\partial^2}{\partial f \partial x}[a(f,x)] + \frac{\partial}{\partial x}[a(f,x)] \cdot \frac{1}{f} - 4\frac{\partial \alpha(f,x)}{\partial f} \quad (4)$$

Multiplying both sides by f and arranging gives the following equation:

$$f \cdot \frac{\partial \alpha(f,x)}{\partial f} = -\frac{f}{4} \cdot \frac{\partial^2 \ln I(f,x)}{\partial f \cdot \partial x} + \frac{1}{4}\left[\frac{\partial a(f,x)}{\partial x} + \frac{\partial^2 a(f,x)}{\partial f \cdot \partial x} \cdot f \cdot \ln f\right] \quad (5)$$

Subjecting both sides of Eq. (3) to a second order partial differentiation with respect to nf, namely the log of the frequency, provides the following equation:

$$\frac{\partial^2 \alpha(f,x)}{\partial (\ln f)^2} = -\frac{1}{4} \cdot \frac{\partial^3 \ln I(f,x)}{\partial (\ln f)^2 \partial x} + \frac{1}{4}\left[2 \cdot \frac{\partial^2 a(f,x)}{\partial (\ln f)\partial x} + \frac{\partial^3 a(f,x)}{\partial^2 (\ln f)\partial x} \cdot \ln f\right] \quad (6)$$

If the ultrasonic attenuation coefficient of the object under investigation is proportional to the power $\beta(x)$ of the frequency, $\alpha(f,x) = \alpha_o(x) f^{\beta(x)}$ will hold, so that the left side of Eq. (5) will become as follows:

$$f \cdot \frac{\partial \alpha(f,x)}{\partial f} = \beta(x) \cdot \alpha(f,x) \quad (7)$$

The left side of Eq. (6) takes on the following form, noting that $\partial/\partial \ln f = f \cdot \partial/\partial f$ holds:

$$\frac{\partial^2 \alpha(f,x)}{\partial (\ln f)^2} = \beta(x)^2 \cdot \alpha(f,x) \quad (8)$$

Dividing Eq. (8) by Eq. (7) gives us:

$$\beta(x) = \frac{\partial^2 \alpha(f,x)}{\partial (\ln f)^2} / f \cdot \frac{\partial \alpha(f,x)}{\partial f} \quad (9)$$

and dividing the square of Eq. (7) by Eq. (8) gives us:

$$\alpha(f,x) = \left[f \cdot \frac{\partial \alpha(f,x)}{\partial f}\right]^2 / \frac{\partial^2 \alpha(f,x)}{\partial (\ln f)^2} \quad (10)$$

whereby the attenuation coefficient $\alpha(f,x)$ and the frequency dependence $\beta(x)$ thereof can be found. That is, by using the following relation:

$$\beta(x) = \frac{\left[-\frac{1}{4} \cdot \frac{\partial^3 \ln I(f,x)}{\partial (\ln f)^2 \partial x} + \frac{1}{4}\left(2 \cdot \frac{\partial^2 a(f,x)}{\partial (\ln f) \cdot \partial x} + \frac{\partial^3 a(f,x)}{\partial^2 (\ln f) \cdot \partial x} \cdot \ln f\right)\right]}{\left[-\frac{f}{4} \cdot \frac{\partial^2 \ln I(f,x)}{\partial f \partial x} + \frac{1}{4}\left(\frac{\partial a(f,x)}{\partial x} + \frac{\partial^2 a(f,x)}{\partial f \partial x} \cdot f \cdot \ln f\right)\right]} \quad (11)$$

derived from Eq. (9) and Eqs. (5), (6), as well as the relation $\alpha(f,x) = \alpha_o(x) f^{\beta(x)}$ obtained from $\beta(x)$ in Eq. (9) and $\alpha(f,x)$ in Eq. (10), $\alpha_o(x)$ may be found from the equation $\alpha_o(x) = \alpha(f,x)/f^{\beta(x)}$.

While the first term in the numerator and denominator of Eq. (11) is a measured quantity, the second term is not a measured quantity and is dependent upon the intensity of reflection at an acoustic characteristic discontinuity surface. This term is a source of error when obtaining $\beta(x)$.

If the coefficient a(f,x) indicating the frequency dependence of the reflection intensity is constant within the range of frequencies measured, that is, if $\partial a(f,x)/\partial f = 0$ holds, then a(f,x) will be a function solely of x (the assumption will be a(x) hereafter), so that Eqs. (5) and (6) may be written as follows, respectively:

$$f \cdot \frac{\partial \alpha(f,x)}{\partial f} = -\frac{f}{4} \cdot \frac{\partial^2 \ln I(f,x)}{\partial f \partial x} + \frac{1}{4}\left[\frac{\partial a(x)}{\partial x}\right] \quad (12)$$

$$\frac{\partial^2 \alpha(f,x)}{\partial (\ln f)^2} = -\frac{1}{4} \cdot \frac{\partial^3 \ln I(f,x)}{\partial (\ln f)^2 \partial x} \quad (13)$$

Therefore, Eq. (11) may be written as follows from Eqs. (12), (13):

$$\beta(x) = \left[-\frac{1}{4} \cdot \frac{\partial^3 \ln I(f,x)}{\partial (\ln f)^2 \partial x}\right] / \left[-\frac{f}{4} \cdot \frac{\partial^2 \ln I(f,x)}{\partial f \partial x} + \frac{1}{4} \cdot \frac{\partial a(x)}{\partial x}\right] \quad (14)$$

Likewise, Eq. (10) may be written as follows:

$$\alpha(f,x) = \left[-\frac{f}{4} \cdot \frac{\partial^2 \ln I(f,x)}{\partial f \partial x} + \frac{1}{4} \cdot \frac{\partial a(x)}{\partial x}\right]^2 / \left[-\frac{1}{4} \cdot \frac{\partial^3 \ln I(f,x)}{\partial (\ln f)^2 \partial x}\right] \quad (15)$$

It will be understood that these have fewer error terms in comparison with Eqs. (11) and (10). In other words, the error in Eq. (14) is solely $$\frac{1}{4} \cdot \frac{\partial a(x)}{\partial x}$$

in the denominator, and in Eq. (15) the error term is solely $$\frac{1}{4} \cdot \frac{\partial a(x)}{\partial x}$$

in the numerator. Furthermore, if the coefficient a(x) is constant and independent of the distance x, then, from $\partial a(x)/\partial x = 0$, Eq. (14) will not contain an error, as indicated by the following equation:

$$\beta(x) = \frac{\partial^3 \ln I(f,x)}{\partial (\ln f)^2 \partial x} / f \cdot \frac{\partial^2 \ln I(f,x)}{\partial f \partial x} \quad (16)$$

In other words, if the coefficient a(f,x) indicating the frequency dependence of the reflection intensity is constant and independent of the measured range of frequency F and of the distance x, then the frequency dependence will be $f^a$, and the frequency dependence $\beta(x)$ of the attenuation coefficient $\alpha(f,x)$ can be calculated accurately by using Eq. (16). In this case, it is also possible to accurately calculate $\alpha(f,x)$, as shown by the following equation, based on Eq. (15):

$$\alpha(f,x) = \frac{f^2}{4} \left[ \frac{\partial^2 \ln I(f,x)}{\partial f \partial x} \right]^2 \Big/ \frac{\partial^3 \ln I(f,x)}{\partial (\ln f)^2 \partial x} \quad (17)$$

The case described above is one in which the echo signal intensity I(f,x) is obtained continuously with relation to the distance x and frequency f. In an actual measurement, however, the echo signal is obtained discretely based upon the given positions of the scatterers. Accordingly, some correction is necessary.

More specifically, differences must be used in place of the differentials employed in Eqs. (5) and (6). As shown in FIG. 1, taking $x_1$ and $x_2$ as the positions at which the scatterers 2, 3 discretely reside, the difference in Eq. (2) between these two positions is obtained and a transformation is made, giving the following equation:

$$\int_{x_1}^{x_2} \alpha(f,x) dx = -\frac{1}{4} \ln[I(f,x_2)/I(f,x_1)] + \frac{1}{4}[a(f,x_2) - a(f,x_1)]\ln f + \frac{1}{4} \ln[g(x_2) \cdot x^{b(x_2)}/g(x_1) \cdot x_1^{b(x_1)}] \quad (18)$$

To obtain an approximate expression corresponding to Eq. (4) by numerical differentiation, we take the difference in Eq. (18) at two frequencies $f_1$, $f_3$, multiply by $$\frac{1}{(f_3 - f_1)(x_2 - x_1)}$$

and arrange to arrive at the following equation:

$$\frac{1}{(x_2 - x_1) \cdot (f_3 - f_1)} \int_{x_1}^{x_2} [\alpha(f_3,x) - \alpha(f_1,x)] dx = \quad (19)$$

$$\frac{1}{4(x_2 - x_1) \cdot (f_3 - f_1)} \ln \left[ \frac{I(f_3,x_1)}{I(f_3,x_2)} \Big/ \frac{I(f_1,x_1)}{I(f_1,x_2)} \right] +$$

$$\frac{1}{4(x_2 - x_1) \cdot (f_3 - f_1)} [\{a(f_3,x_2) - a(f_3,x_1)\}\ln f_3 -$$

$$\{a(f_1,x_2) - a(f_1,x_1)\}\ln f_1]$$

To obtain an appoximate expression corresponding to Eq. (5), we multiply by $(f_3+f_1)/2$ to arrive at the following equation:

$$H_2 = \frac{f_3 + f_1}{2(x_2 - x_1) \cdot (f_3 - f_1)} \int_{x_1}^{x_2} [\alpha(f_3,x) - \alpha(f_1,x)] dx \quad (20)$$

$$= \frac{f_3 + f_1}{8(x_2 - x_1) \cdot (f_3 - f_1)} \cdot \ln \left[ \frac{I(f_3,x_1)}{I(f_3,x_2)} \Big/ \frac{I(f_1,x_1)}{I(f_1,x_2)} \right] + D_2,$$

where $$D_2 = \frac{f_3 + f_1}{8(x_2 - x_1) \cdot (f_3 - f_1)} [\{a(f_3,x_2) - a(f_3,x_1)\}\ln f_3 -$$

$$\{a(f_1,x_2) - a(f_1,x_1)\}\ln f_1]$$

From $\alpha(f,x) = \alpha_o(x) f^{\beta(x)}$ we have:

$$\frac{f_3 + f_1}{2(x_2 - x_1) \cdot (f_3 - f_1)} \int_{x_1}^{x_2} [\alpha(f_3,x) - \alpha(f_1,x)] dx =$$

$$\frac{f_3 + f_1}{2(x_2 - x_1) \cdot (f_3 - f_1)} \int_{x_1}^{x_2} \alpha_o(x)[f_3^{\beta(x)} - f_1^{\beta(x)}] dx$$

which gives us the following:

$$H_2 \approx \frac{1}{x_2 - x_1} \int_{x_1}^{x_2} \beta(x) \cdot \alpha\left(\frac{f_1 + f_3}{2}, x\right) dx \quad (21)$$

Likewise, to obtain an approximate expression corresponding to Eq. (6) by numerical differentiation, we use data regarding three frequencies $f_1$, $f_2$, $f_3$ ($f_1 < f_2 < f_3$), take a difference quotient of second order with relation to the frequency logarithms $\ln f_1$, $\ln f_2$, $\ln f_3$, and make a transformation to obtain the following equation:

$$H_3 = \frac{A}{x_2 - x_1} \int_{x_1}^{x_2} \left[ \alpha(f_1,x)\ln\frac{f_2}{f_3} + \alpha(f_2,x) \cdot \ln\frac{f_3}{f_1} + \alpha(f_3,x) \cdot \ln\frac{f_1}{f_2} \right] dx \quad (22)$$

$$= \frac{-A}{4(x_2 - x_1)} \left[ \ln\frac{I(f_1,x_2)}{I(f_1,x_1)} \cdot \ln\frac{f_2}{f_3} + \ln\frac{I(f_2,x_2)}{I(f_2,x_1)} \cdot \ln\frac{f_3}{f_1} + \ln\frac{I(f_3,x_2)}{I(f_3,x_1)} \cdot \ln\frac{f_1}{f_2} \right] + D_3$$

where $$D_3 = \frac{-A}{4(x_2 - x_1)} \left[ \{a(f_1,x_2) - a(f_1,x_1)\}\ln f_1 \cdot \ln\frac{f_2}{f_3} + \{a(f_2,x_2) - a(f_2,x_1)\}\ln f_2 \cdot \ln\frac{f_3}{f_1} + \{a(f_3,x_2) - a(f_3,x_1)\}\ln f_3 \cdot \ln\frac{f_1}{f_2} \right]$$

and $$A = 2/\{\ln(f_1/f_2)\ln(f_2/f_3)\ln(f_1/f_3)\}$$

Therefore, we have the following:

$$H_3 \approx \frac{1}{x_2 - x_1} \int_{x_1}^{x_2} \beta^2(x) \cdot \alpha\left(\frac{f_1 + f_2 + f_3}{3}, x\right) dx \quad (23)$$

Dividing Eq. (23) by Eq. (21) gives the following equation:

$$\frac{H_3}{H_2} \approx \int_{x_1}^{x_2} \beta^2(x) \cdot \alpha\left(\frac{f_1 + f_2 + f_3}{3}, x\right) dx \Big/ \int_{x_1}^{x_2} \beta^2(x) \cdot \alpha\left(\frac{f_1 + f_3}{2}, x\right) dx \quad (24)$$

Thus, Eq. (24) corresponds to Eq. (9) and gives an approximate expression of a mean value of $\beta(x)$ between $x_1$ and $x_2$. $H_3/H_2$ takes on the following form from Eqs. (20), (22):

$$\frac{H_3}{H_2} = \frac{-\frac{A}{4(x_2-x_1)}\left[\ln\frac{I(f_1,x_2)}{I(f_1,x_1)}\cdot\ln\frac{f_2}{f_3} + \ln\frac{I(f_2,x_2)}{I(f_2,x_1)}\cdot\ln\frac{f_3}{f_1} + \ln\frac{I(f_3,x_2)}{I(f_3,x_1)}\cdot\ln\frac{f_1}{f_2}\right] + D_3}{\frac{f_3+f_1}{8(x_2-x_1)\cdot(f_3-f_1)}\cdot\ln\left[\frac{I(f_3,x_1)}{I(f_3,x_2)}\bigg/\frac{I(f_1,x_1)}{I(f_1,x_2)}\right] + D_2} \quad (25)$$

where $$D_3 = \frac{-A}{4(x_2-x_1)}\left[\{a(f_1,x_2)-a(f_1,x_1)\}\ln f_1\cdot\ln\frac{f_2}{f_3} + \{a(f_2,x_2)-a(f_2,x_1)\}\ln f_2\cdot\ln\frac{f_3}{f_1} + \{a(f_3,x_2)-a(f_3,x_1)\}\ln f_3\cdot\ln\frac{f_1}{f_2}\right]$$

$$D_2 = \frac{f_3+f_1}{8(x_2-x_1)\cdot(f_3-f_1)}[\{a(f_3,x_2)-a(f_3,x_1)\}\ln f_3 - \{a(f_1,x_2)-a(f_1,x_1)\}\ln f_1]$$

Further, from Eqs. (21) and (23) we have:

$$\frac{H_2^2}{H_3} \approx \left\{\int_{x_1}^{x_2}\beta(x)\alpha\left(\frac{f_1+f_2}{2},x\right)dx\right\}^2 \bigg/ \int_{x_1}^{x_2}\beta(x)\cdot\alpha\left(\frac{f_1+f_2+f_3}{3},x\right)dx \quad (26)$$

Thus, Eq. (26) corresponds to Eq. (10) and gives a mean value of $\alpha(f,x)$ between $x_1$ and $x_2$ and between $f_1$ and $f_3$. $(H_2)^2/H_3$ takes on the following form from Eqs. (20), (22):

$$\frac{H_2^2}{H_3} = \frac{\left\{\frac{f_3+f_1}{8(x_2-x_1)(f_3-f_1)}\cdot\ln\left[\frac{I(f_3,x_1)}{I(f_3,x_2)}\bigg/\frac{I(f_1,x_1)}{I(f_1,x_2)}\right] + D_2\right\}^2}{\frac{-A}{4(x_2-x_1)}\left[\ln\frac{I(f_1,x_2)}{I(f_1,x_1)}\cdot\ln\frac{f_2}{f_3} + \ln\frac{I(f_2,x_2)}{I(f_2,x_1)}\ln\frac{f_3}{f_1} + \ln\frac{I(f_3,x_2)}{I(f_3,x_1)}\ln\frac{f_1}{f_2} + D_3\right]} \quad (27)$$

The first term in the denominator of Eq. (25) and the first term in the numerator thereof are measured quantities, as in Eq. (11), but the second terms, namely $D_2$ and $D_3$, arise owing to frequency dependence ascribable to the intensity of reflection at the acoustic characteristic discontinuity surface, also as in Eq. (11). These represent error terms with respect to $\beta(x)$. If the coefficient $a(f,x)$ of the frequency dependence $f^{a(f,x)}$ of the reflection intensity is constant within the range of frequencies measured, namely if $a(f_1,x_1)=a(f_2,x_1)=a(f_3,x_1)=a(x_1)$ and $a(f_1,x_2)=a(f_2,x_2)=a(f_3,x_2)=a(x_2)$ hold, then a will be a function solely of x and $D_3$ will be zero. Accordingly, Eqs. (20), (22) may then be written as follows:

$$H_2 = \frac{f_3+f_1}{2(x_2-x_1)(f_3-f_1)}\int_{x_1}^{x_2}[a(f_3,x)-a(f_1,x)]dx \quad (28)$$

$$= \frac{f_3+f_1}{8(x_2-x_1)(f_3-f_1)}\ln\left[\frac{I(f_3,x_1)}{I(f_3,x_2)}\bigg/\frac{I(f_1,x_1)}{I(f_1,x_2)}\right] +$$

-continued $$\frac{f_3+f_1}{8(x_2-x_1)(f_3-f_1)}\left[\{a(x_2)-a(x_1)\}\ln\frac{f_3}{f_1}\right]$$

$$H_3 = \frac{-A}{4(x_2-x_1)}\left\{\ln\frac{I(f_1,x_2)}{I(f_1,x_1)}\cdot\ln\frac{f_2}{f_3} + \ln\frac{I(f_2,x_2)}{I(f_2,x_1)}\cdot\ln\frac{f_3}{f_1} + \ln\frac{I(f_3,x_2)}{I(f_3,x_1)}\cdot\ln\frac{f_1}{f_2}\right\} \quad (29)$$

Therefore, Eq. (25) takes on the following form from Eqs. (28) and (29):

$$\beta(x) = \frac{H_3}{H_2} \quad (30)$$

$$= \frac{-2A(f_3-f_1)\cdot\left[\ln\frac{I(f_1,x_2)}{I(f_1,x_1)}\cdot\ln\frac{f_2}{f_3} + \ln\frac{I(f_2,x_2)}{I(f_2,x_1)}\cdot\ln\frac{f_3}{f_1} + \ln\frac{I(f_3,x_2)}{I(f_3,x_1)}\ln\frac{f_1}{f_2}\right]}{(f_3+f_1)\left[\ln\left(\frac{I(f_3,x_1)}{I(f_3,x_2)}\bigg/\frac{I(f_1,x_1)}{I(f_1,x_2)}\right) + \{a(x_2)-a(x_1)\}\cdot\ln\frac{f_3}{f_1}\right]} \quad (30)$$

And Eq. (27) takes on the following form from Eqs. (28) and (29):

$$a(f,x) \approx \frac{H_2^2}{H_3} = -\frac{1}{16A}\left[\frac{f_3+f_1}{(x_2-x_1)(f_3-f_1)}\right]^2 \cdot$$

$$\frac{\left[\ln\left(\frac{I(f_3,x_1)}{I(f_3,x_2)}\bigg/\frac{I(f_1,x_1)}{I(f_1,x_2)}\right) + \{a(x_2)-a(x_1)\}\ln\frac{f_3}{f_1}\right]^2}{\left\{\ln\frac{I(f_1,x_2)}{I(f_1,x_1)}\cdot\ln\frac{f_2}{f_3} + \ln\frac{I(f_2,x_2)}{I(f_2,x_1)}\ln\frac{f_3}{f_1} + \ln\frac{I(f_3,x_2)}{I(f_3,x_1)}\ln\frac{f_1}{f_2}\right\}} \quad (31)$$

It may be understood that these two equations have fewer error terms in comparison with Eqs. (25) and (27). More specifically, the error term in Eq. (30) is solely $[a(x_2)-a(x_1)]\cdot\ln(f_3/f_1)$ in the denominator, and the error term in Eq. (31) is solely $[a(x_2)-a(x_1)]\cdot\ln(f_3/f_1)$ in the numerator.

If the coefficient a(x) of the frequency dependence $f^{a(x)}$ of the reflection intensity is constant and independent of the distance x, then, from $a(x_2)=a(x_1)$, Eq. (30) may be written as the following equation, in which the error is reduced even further:

$$\beta(x) \approx \frac{H_3}{H_2} \tag{32}$$

$$= -2A \cdot \frac{(f_3 - f_1)\left[\ln\frac{I(f_1,x_2)}{I(f_1,x_1)} \ln\frac{f_2}{f_3} + \ln\frac{I(f_2,x_2)}{I(f_2,x_1)} \ln\frac{f_3}{f_1} + \ln\frac{I(f_3,x_2)}{I(f_3,x_1)} \ln\frac{f_1}{f_2}\right]}{(f_3 + f_1) \cdot \ln\left[\frac{I(f_3,x_1)}{I(f_3,x_2)} \Big/ \frac{I(f_1,x_1)}{I(f_1,x_2)}\right]}$$

In other words, if the coefficient a(f,x) indicating the frequency dependence of the reflection intensity is constant and independent of the frequency f within the measured range and of the distance x, then $a(f,x)=a$ will hold and, in accordance with Eq. (32), the mean value $\beta(x)$ of the frequency dependence of the attenuation coefficient $\alpha(f,x)$ can be measured with even greater accuracy. In this case, in accordance with Eq. (31), it is also possible to measure $\alpha(f,x)$ with greater accuracy as shown by the following equation:

$$\alpha(f,x) = -\frac{1}{16A}\left[\frac{f_3+f_1}{(x_2-x_1)(f_3-f_1)}\right]^2 \cdot \tag{33}$$

$$\frac{\left[\ln\frac{I(f_3,x_1)}{I(f_3,x_2)} \Big/ \frac{I(f_1,x_1)}{I(f_1,x_2)}\right]^2}{\ln\frac{I(f_1,x_2)}{I(f_1,x_1)} \cdot \ln\frac{f_2}{f_3} + \ln\frac{I(f_2,x_2)}{I(f_2,x_1)} \cdot \ln\frac{f_3}{f_1} + \ln\frac{I(f_3,x_2)}{I(f_3,x_1)} \ln\frac{f_1}{f_2}}$$

In this case, $\alpha_o(x)$ also is obtained with greater accuracy.

Thus, as set forth above, ultrasonic pulses having frequencies of $f_1$, $f_2$, $f_3$ are projected into the object and $\alpha$, $\alpha_o$, $\beta$ can be calculated from the reflection intensity of these pulses.

In Eqs. (20), (22), $D_2$ and $D_3$ are error terms which cannot be found from measured values. In Eq. (20) $D_2$ vanishes when a(f,x) is constant and independent of $f_1$, $f_3$, $x_1$, $x_2$. In Eq. (22), $D_3$ vanishes when a(f,x) is constant with regard to the frequencies $f_1$, $f_2$, $f_3$ even if it is dependent upon $x_1$, $x_2$. In cases where the foregoing conditions do not hold, however, the relative error can be evaluated in the following way. Specifically, since $0 \leq a(f,x) \leq 4$ holds, we may write:

$$|D_2| = \left|\frac{f_3+f_1}{8(x_2-x_1)(f_3-f_1)}[\{a(f_3,x_2) - a(f_3,x_1)\}\ln f_3 - \right.$$

$$\left.\{a(f_1,x_2) - a(f_1,x_1)\}\ln f_1]\right| \leq \frac{f_3+f_1}{|8(x_2-x_1)(f_3-f_1)|}\left|4\ln f_3 - 4\ln f_1\right| = \frac{f_3+f_1}{2|x_2-x_1||f_3-f_1|}\left|\ln\frac{f_3}{f_1}\right|$$

Therefore, we have the following relation:

$$\left|\frac{D_2}{H_2}\right| \leq \frac{f_3+f_1}{2|f_3-f_1|}\left|\ln\frac{f_3}{f_1}\right| \Big/ \int_{x_1}^{x_2}\beta(x)\alpha\left(\frac{f_1+f_3}{2},x\right)dx \tag{34}$$

This gives the relative error ascribable to $D_2$ in Eq. (20). Likewise, we have:

$$\left|\frac{D_3}{H_3}\right| \leq \tag{35}$$

$$\frac{2\text{Max}\left[\left|\ln f_1 \cdot \ln\frac{f_2}{f_3}\right|, \left|\ln f_3 \cdot \ln\frac{f_1}{f_2}\right|\right]}{\left|\int_{x_1}^{x_2}\beta^2(x)\alpha\left(\frac{f_1+f_2+f_3}{3},x\right)dx\right| \cdot \left|\ln\frac{f_1}{f_2} \cdot \ln\frac{f_2}{f_3} \cdot \ln\frac{f_1}{f_3}\right|}$$

This gives the relative error ascribable to $D_3$ in Eq. (22). In conclusion, the error terms $D_2$, $D_3$ can be neglected if, from Eqs. (34), (35), the value of the following is sufficiently large:

$$\int_{x_1}^{x_2}\beta(x)\alpha\left(\frac{f_1+f_3}{2},x\right)dx;$$

$$\int_{x_1}^{x_2}\beta^2(x)\alpha\left(\frac{f_1+f_2+f_3}{3},x\right)dx$$

As set forth above, attenuation coefficients $\alpha(f,x)$, $\alpha_o(x)$ and their frequency dependence $\beta(x)$ can be approximately measured by three different frequencies $f_1$, $f_2$, $f_3$. In particular, if the coefficient a(f,x) is constant and independent of the observed range of frequency f and of the distance x, then it is possible to measure $\alpha(f,x)$, $\alpha_o(x)$ and (x) with greater accuracy.

In actuality, however, the coefficient a(f,x) indicative of frequency dependence of the reflection intensity is an unknown quantity. Therefore, the actual calculation of $\alpha(f,x)$, $\alpha_o(x)$ and $\beta(x)$ is performed from $H_2$ and $H_3$ in the following equations based on measured quantity I(f,x):

$$H_2 = \frac{f_3+f_1}{8(x_2-x_1)(f_3-f_1)}\ln\left[\frac{I(f_3,x_1)}{I(f_3,x_2)} \Big/ \frac{I(f_1,x_1)}{I(f_1,x_2)}\right] \tag{28'}$$

$$H_3 = \frac{-A}{4(x_2-x_1)}\left[\ln\frac{I(f_1,x_2)}{I(f_1,x_1)}\ln\frac{f_2}{f_3} + \ln\frac{I(f_2,x_2)}{I(f_2,x_1)}\ln\frac{f_3}{f_1} + \right. \tag{29}$$

$$\ln \frac{I(f_3, x_2)}{I(f_3, x_1)} \ln \frac{f_1}{f_2} \Bigg]$$

In the following, we will discuss the case in which the ultrasonic beam is emitted into the object comprising the tissues of which coefficient a(f,x) is proportional to frequency f, namely $a(f,x) = a_o(x) \cdot f$ holds.

We start with Eq.(2) again. To facilitate the mathematical perspective, we assume the echo intensity I(f,x) is obtained continuously with regard to the distance x and frequency f. Performing a first order partial differentiation with respect to f·ln f gives us:

$$\frac{\partial \ln I(f,x)}{\partial (f \cdot \ln f)} = \frac{\partial \ln I_o(f)}{\partial (\ln f)} + \frac{\partial a(f,x)}{\partial (\ln f)} \ln f + \quad (36)$$

$$\frac{a(f,x)}{f(1 + \ln f)} - 4 \int_0^x \frac{\partial a(f,x)}{\partial (f \cdot \ln f)} dx$$

Subjecting both sides of Eq.(36) to a first order partial diffentiation with respect to x and arranging give us the following equation:

$$\frac{\partial a(f,x)}{\partial (\ln f)} = -\frac{1}{4} \frac{\partial^2 \ln I(f,x)}{\partial x \partial (\ln f)} + J_2, \quad (37)$$

where $$J_2 = \frac{1}{4} \cdot \frac{\partial^2 a(f,x)}{\partial x \partial (\ln f)} \ln f + \frac{1}{4} \frac{1}{f(1 + \ln f)} \frac{\partial a(f,x)}{\partial x}$$

Subjecting both sides of Eq.(37) to partial differentiation with respect to f·lnf provides the following equation:

$$\frac{\partial^2 a(f,x)}{\partial (\ln f)^2} = -\frac{1}{4} \frac{\partial^3 \ln I(f,x)}{\partial x \partial (\ln f)^2} + J_3, \quad (38)$$

where $$J_3 = \frac{\partial J_2}{\partial (\ln f)} = \frac{1}{4} \frac{\partial^3 a(f,x)}{\partial x \partial (\ln f)^2} \cdot \ln f +$$

$$\frac{1}{2f(1 + \ln f)} \cdot \frac{\partial^2 a(f,x)}{\partial x \partial (\ln f)} + \frac{1}{4} \frac{2 + \ln f}{f^2(1 + \ln f)^3} \cdot \frac{\partial a(f,x)}{\partial x}$$

Assuming the following equation as described previously holds:
$$a(f,x) = a_o(x) \cdot f^{\beta(x)} \quad (39)$$

We get the equation as follows:

$$\frac{\partial a(f,x)}{\partial (\ln f)} = \frac{\partial a_o(x) f^{\beta(x)}}{\partial f} \cdot \frac{\partial f}{\partial (\ln f)} = \frac{\beta(x) a(f,x)}{f(1 + \ln f)} \quad (40)$$

Thus, the left side of Eq.(38) will become as follows:

$$\frac{\partial^2 a(f,x)}{\partial (\ln f)^2} = \frac{\partial}{\partial (\ln f)} \frac{\beta(x) a(f,x)}{f(1 + \ln f)} \quad (41)$$

$$= \frac{\beta(x) a(f,x) [(\beta(x) - 1)(1 + \ln f) - 1]}{f^2 (1 + \ln f)^3}$$

Dividing Eq.(41) by Eq.(40) gives us;

$$\beta(x) = f(1 + \ln f) \left[ \frac{\partial^2 a(f,x)}{\partial (\ln f)^2} \bigg/ \frac{\partial a(f,x)}{\partial (\ln f)} \right] + \frac{2 + \ln f}{1 + \ln f} \quad (42)$$

We get the following equation from Eq.(42) and Eq.(40).

$$a(f,x) = \frac{\frac{\partial a(f,x)}{\partial (\ln f)}}{\left[ \frac{\partial^2 a(f,x)}{\partial (\ln f)^2} \bigg/ \frac{\partial a(f,x)}{\partial (\ln f)} \right] + \frac{2 + \ln f}{f(1 + \ln f)^2}} \quad (43)$$

Thus, the attenuation coefficient a(f,x) and the frequency dependence β(x) of the coefficient a(f,x) can be calculated as follows by using Eq.(42), Eq.(37) and Eq.(38):

$$\beta(x) = f(1 + \ln f) \cdot \quad (44)$$

$$\frac{\left[ -\frac{1}{4} \frac{\partial^3 \ln I(f,x)}{\partial x \partial (\ln f)^2} + \frac{1}{4} \frac{\partial^3 a(f,x)}{\partial x \partial (\ln f)^2} \cdot \ln f + \right.}{\left[ -\frac{1}{4} \frac{\partial^2 \ln I(f,x)}{\partial x \partial (\ln f)} + \frac{1}{4} \frac{\partial^2 a(f,x)}{\partial x \partial (\ln f)} \cdot \ln f + \right.}$$

$$\left. \frac{1}{2} \frac{1}{f(1+\ln f)} \frac{\partial^2 a(f,x)}{\partial x \partial (\ln f)} + \frac{1}{4} \frac{2 + \ln f}{f^2(1+\ln f)^3} \frac{\partial a(f,x)}{\partial x} \right]$$
$$\left. \frac{1}{4} \frac{1}{f(1+\ln f)} \frac{2 a(f,x)}{\partial x} \right] +$$

$$\frac{2 + \ln f}{1 + \ln f}$$

From Eq.(43), Eq.(37), (38), we have:

$$a(f,x) = \frac{-\frac{1}{4} \frac{\partial^2 \ln I(f,x)}{\partial x \partial (\ln f)} + J_2}{\left[ -\frac{1}{4} \frac{\partial^3 \ln I(f,x)}{\partial x \partial (\ln f)^2} + J_3 \right] \bigg/ \left[ -\frac{1}{4} \frac{\partial^2 \ln I(f,x)}{\partial x \partial (\ln f)} + J_2 \right] + \frac{2 + \ln f}{f(1 + \ln f)^2}} \quad (45)$$

From β(x) in Eq.(42) and a(f,x) in Eq.(43), we can calculate $a_o(x)$ by using the equation $a(f,x) = a_o(x) \cdot f^{\beta(x)}$.

While the first term in the numerator and the denominator of Eq.(44) is a measured quantity, the terms on and after the second are derived from the intensity of reflection at an acoustic characteristic discontinuity surface and are a source of error when obtaining β(x).

If the coefficient a(f,x) is constant within the measured range of frequencies, that is, if $a(f,x) = 0$ hold, then a(f,x) will be a function solely of x, so that Eqs. (37) and (38) may be written as follows, respectively:

$$\frac{\partial a(f,x)}{\partial (\ln f)} = -\frac{1}{4} \frac{\partial^2 \ln I(f,x)}{\partial x \partial (\ln f)} + \frac{1}{4f(1 + \ln f)} \frac{\partial a(f,x)}{\partial x} \quad (46)$$

$$\frac{\partial^2 a(f,x)}{\partial (\ln f)^2} = -\frac{1}{4} \frac{\partial^3 \ln I(f,x)}{\partial x \partial (\ln f)^2} + \frac{2 + \ln f}{4f^2(1 + \ln f)^3} \frac{\partial a(f,x)}{\partial x} \quad (47)$$

Therefore, Eq.(44) may be written from Eqs.(46) and (47) as follows:

$$\beta(x) = f(1 + \ln f) \cdot \quad (48)$$

$$\frac{-\frac{1}{4} \frac{\partial^3 \ln I(f,x)}{\partial x \partial (\ln f)^2} + \frac{1}{4} \frac{2 + \ln f}{f^2(1 + \ln f)^3} \frac{\partial a(f,x)}{\partial x}}{-\frac{1}{4} \frac{\partial^2 \ln I(f,x)}{\partial x \partial (\ln f)} + \frac{1}{4f(1 + \ln f)} \frac{\partial a(f,x)}{\partial x}}$$

Likewise, we have the following equation from Eq.(45):

$$a(f,x) = \frac{\left[-\frac{1}{4} \frac{\partial^2 \ln I(f,x)}{\partial x \partial (\ln f)} + \frac{1}{4f(1 + \ln f)} \frac{\partial a(f,x)}{\partial x}\right]}{\left[-\frac{1}{4} \frac{\partial^3 \ln I(f,x)}{\partial x \partial (\ln f)^2} + \frac{2 + \ln f}{4f^2(1 + \ln f)^3} \frac{\partial a(f,x)}{\partial x}\right] / \left[-\frac{1}{4} \frac{\partial^2 \ln I(f,x)}{\partial x \partial (\ln f)} + \frac{1}{4f(1 + \ln f)} \frac{\partial a(f,x)}{\partial x}\right] + \frac{2 + \ln f}{f(1 + \ln f)^2}} \quad (49)$$

It will be understood that these Eqs.(48),(49) have fewer error terms in comparison with Eqs.(43) and (44).

If a(x) is constant and independent of distance x, Eq.(48) will not contain an error, as indicated by the following equation:

$$\beta(x) = f(1 + \ln f) \left[\frac{\partial^3 \ln I(f,x)}{\partial x \partial (\ln f)^2} / \frac{\partial^2 \ln I(f,x)}{\partial x \partial (\ln f)}\right] \quad (50)$$

In other words, if the coefficient a(f,x) indicating the frequency dependence of the reflection intensity is constant and independent of the measured range of frequency f and the distance x, then the frequency dependence will be $f^a$, and the frequency dependence $\beta(x)$ of the attenuation coefficient $a(f,x)$ can be calculated accurately by using Eq.(50). In this case, it is also possible to accurately calculate $a(f,x)$ as shown by the following equation, based on Eq.(49):

$$a(f,x) = \quad (51)$$

$$\frac{-\frac{1}{4} \frac{\partial^2 \ln I(f,x)}{\partial x \partial (\ln f)}}{\left[-\frac{1}{4} \frac{\partial^3 \ln I(f,x)}{\partial x \partial (\ln f)^2}\right] / \left[-\frac{1}{4} \frac{\partial^2 \ln I(f,x)}{\partial x \partial (\ln f)}\right] + \frac{2 + \ln f}{f(1 + \ln f)^2}}$$

Next, we will discuss the case in which the coefficient a(f,x) is not constant but proportional to frequency f within the range of frequencies measured. In such case, we can assume that $a(f,x) = a_0(x) \cdot f$, thus obtaining the following Eqs.(37) and (38):

$$\frac{\partial a(f,x)}{\partial (\ln f)} = -\frac{1}{4} \frac{\partial^2 \ln I(f,x)}{\partial x \partial (\ln f)} + \frac{1}{4} \frac{\partial a_0(x)}{\partial x} \quad (52)$$

$$\frac{\partial^2 a(f,x)}{\partial (\ln f)^2} = -\frac{1}{4} \frac{\partial^3 \ln I(f,x)}{\partial x \partial (\ln f)^2} \quad (53)$$

Therefore, Eq.(44) will become from Eqs.(52) and (53) as follows:

$$\beta(x) = f(1 + \ln f) \cdot \quad (54)$$

$$\frac{-\frac{1}{4} \frac{\partial^3 \ln I(f,x)}{\partial x \partial (\ln f)^2}}{-\frac{1}{4} \frac{\partial^2 \ln I(f,x)}{\partial x \partial (\ln f)} + \frac{1}{4} \frac{\partial a_0(x)}{\partial x}} + \frac{2 + \ln f}{1 + \ln f}$$

Likewise, Eq.(43) will become:

$$a(f,x) = \frac{-\frac{1}{4} \frac{\partial^2 \ln I(f,x)}{\partial x \partial (\ln f)} + \frac{1}{4} \frac{\partial a_0(x)}{\partial x}}{\left[-\frac{1}{4} \frac{\partial^3 \ln I(f,x)}{\partial x \partial (\ln f)^2} / \left\{-\frac{1}{4} \frac{\partial^2 \ln I(f,x)}{\partial x \partial (\ln f)} + \frac{1}{4} \frac{\partial a_0(x)}{\partial x}\right\}\right] + \frac{2 + \ln f}{f(1 + \ln f)^2}} \quad (55)$$

We will find out that Eqs.(54) and (55) have fewer error terms in comparison with Eqs.(44) and (45). In other words, the error term in Eq.(54) is solely $$\frac{1}{4} \cdot \frac{\partial a_0(x)}{\partial x}$$

in the denominator, and the error term in Eq.(55) is solely $$\frac{1}{4} \frac{\partial a_0(x)}{\partial x}$$

in both the denominator and the numerator.

The case described above is one in which the echo signal intensity I(f,x) is obtained continuously with relation to the distance x and frequency f. In an actual measurement, however, echo signal is obtained discretely based upon the given positions of the scatterers. Accordingly, some correction is necessary.

More specifically, differences must be used in place of the differentials employed in Eqs.(37) and (38). As shown in FIG. 1, taking $x_1$ and $x_2$ as the positions at which the scatterers 2, 3 discretely reside, the difference in Eq. (2) between these two positions is obtained and a transformation is made, giving the following equation as well as Eq.(18):

$$\int_{x_1}^{x_2} a(f,x)dx = -\frac{1}{4} \ln \frac{I(f,x_2)}{I(f,x_1)} + \frac{1}{4} [a(f,x_2) - a(f,x_1)]\ln f + \tag{56}$$

$$\frac{1}{4} \ln \frac{g(x_2) \cdot x_2^{b(x_2)}}{g(x_1) \cdot x_1^{b(x_1)}}$$

The equation corresponding to Eq.(37) is as follows:

$$K_2(f_1,f_3) = \frac{1}{x_2 - x_1} \int_{x_1}^{x_2} \frac{a(f_1,x) - a(f_3,x)}{f_1 \ln f_1 - f_3 \ln f_3} dx \tag{57}$$

$$= -\frac{1}{4(x_2 - x_1)(f_1 \ln f_1 - f_3 \ln f_3)} \ln \left[ \frac{I(f_1,x_2)}{I(f_1,x_1)} \bigg/ \frac{I(f_3,x_2)}{I(f_3,x_1)} \right] + L_2(f_1,f_3),$$

where $$L_2(f_1,f_3) = \frac{[a(f_1,x_2) - a(f_1,x_1)] \cdot \ln f_1 - [a(f_3,x_2) - a(f_3,x_1)] \cdot \ln f_3}{4(x_2 - x_1)(f_1 \ln f_1 - f_3 \ln f_3)} \tag{58}$$

Likewise, the equation corresponding to Eq.(38) is as follows:

$$K_3(f_1,f_2,f_3) = \frac{K_2(f_1,f_2) - K_2(f_2,f_3)}{\{(f_1\ln f_1 + f_2\ln f_2)/2 - (f_2\ln f_2 + f_3\ln f_3)/2\}} \tag{59}$$

$$= \frac{2}{x_2 - x_1} \int_{x_1}^{x_2} \frac{a(f_1,x)(f_2\ln f_2 - f_3\ln f_3) + a(f_2,x)(f_3\ln f_3 - f_1\ln f_1) + a(f_3,x)(f_1\ln f_1 - f_2\ln f_2)}{(f_1\ln f_1 - f_2\ln f_2)(f_2\ln f_2 - f_3\ln f_3)(f_1\ln f_1 - f_3\ln f_3)} dx$$

$$= -\frac{1}{2(x_2 - x_1)(f_1\ln f_1 - f_2\ln f_2)(f_2\ln f_2 - f_3\ln f_3)(f_1\ln f_1 - f_3\ln f_3)}$$

$$\left\{ \ln \frac{I(f_1,x_2)}{I(f_1,x_1)} \cdot (f_2\ln f_2 - f_3\ln f_3) + \ln \frac{I(f_2,x_2)}{I(f_2,x_1)} \cdot (f_3\ln f_3 - f_1\ln f_1) + \ln \frac{I(f_3,x_2)}{I(f_3,x_1)} (f_1\ln f_1 - f_2\ln f_2) \right\} + L_3(f_1,f_2,f_3),$$

where $$L_3(f_1,f_2,f_3) = \frac{2\{L_2(f_1,f_2) - L_2(f_2,f_3)\}}{f_1\ln f_1 - f_3\ln f_3} \tag{60}$$

$$= \frac{1}{2} \left[ \frac{\{a(f_1,x_2) - a(f_1,x_1)\}\ln f_1(f_2\ln f_2 - f_3\ln f_3) +}{(x_2 - x_1)(f_1\ln f_1 - f_2\ln f_2) \cdot} \right.$$

$$\left. \frac{\{a(f_2,x_2) - a(f_2,x_2)\}\ln f_2(f_3\ln f_3 - f_1\ln f_1) + \{a(f_3,x_2) - a(f_3,x_1)\}\ln f_3(f_1\ln f_1 - f_2\ln f_2)}{(f_2\ln f_2 - f_3\ln f_3)(f_1\ln f_1 - f_3\ln f_3)} \right]$$

We can approximate the left side of Eq.(57) to the following equation, noting $a(f,x) = a_0(x)f^{\beta(x)}$ and Eq.(40):

$$\frac{1}{x_2 - x_1} \int_{x_1}^{x_2} \frac{a(f_1,x) - a(f_3,x)}{f_1\ln f_1 - f_3\ln f_3} dx \approx \tag{61}$$

$$\frac{1}{x_2 - x_1} \int_{x_1}^{x_2} \frac{\beta(x)a((f_3 + f_1)/2,x)dx}{(f_1 + f_3)/2 \cdot (1 + \ln(f_1 + f_3)/2)}$$

Likewise, we approximate the left side of Eq.(59) to the following equation, noting Eq.(41):

$$\frac{1}{x_2 - x_1} \int_{x_1}^{x_2} \left[ \frac{a(f_1,x) - a(f_2,x)}{f_1\ln f_1 - f_2\ln f_2} - \frac{a(f_2,x) - a(f_3,x)}{f_2\ln f_2 - f_3\ln f_3} \right] \frac{2}{f_1 - f_3} dx \approx \tag{62}$$

$$\frac{1}{x_2 - x_1} \int_{x_1}^{x_2} \frac{\beta(x)a\left(\frac{f_1 + f_2 + f_3}{3},x\right)\left[(\beta(x) - 1)\left(1 + \ln\frac{f_1 + f_2 + f_3}{3}\right) - 1\right] dx}{\left(\frac{f_1 + f_2 + f_3}{3}\right)^2 \left(1 + \ln\frac{f_1 + f_2 + f_3}{3}\right)^3}$$

Multiplying both sides of Eq.(61) by $$\frac{f_1 + f_3}{2}\left(1 + \ln\frac{f_1 + f_3}{2}\right)$$

and arranging gives us the following equations instead of Eqs.(57) and (58):

$$K_2'(f_1,f_3) \equiv \left(\frac{f_1+f_3}{2}\right)\left(1+\ln\frac{f_1+f_3}{2}\right)K_2 \approx \quad (63)$$

$$\frac{1}{x_2-x_1}\int_{x_1}^{x_2}\beta(x)\alpha\left(\frac{f_1+f_3}{2},x\right)dx$$

$$= \frac{f_1+f_3}{8(x_2-x_1)(f_1\ln f_1 - f_3\ln f_3)}\left(1+\right.$$

$$\left.\ln\frac{f_1+f_3}{2}\right)\ln\left[\frac{I(f_1,x_1)}{I(f_1,x_2)}\Big/\frac{I(f_3,x_1)}{I(f_3,x_2)}\right] + L_2',$$

where $$L_2' = \frac{f_1+f_3}{8(x_2-x_1)(f_1\ln f_1 - f_3\ln f_3)}\left(1+\ln\frac{f_1+f_3}{2}\right)\cdot$$

$$\{[a(f_1,x_2) - a(f_1,x_1)]\ln f_1 - [a(f_3,x_2) - a(f_3,x_1)]\ln f_3\}$$

Multiplying both sides of Eq.(62) by $$\left(\frac{f_1+f_2+f_3}{3}\right)^2 \cdot \left(1+\ln\frac{f_1+f_2+f_3}{3}\right)^3$$

and arranging give us the following equations instead of Eqs.(59) and (60).

$$K_3'(f_1,f_2,f_3) \equiv \left(\frac{f_1+f_2+f_3}{3}\right)^2\left(1+\ln\frac{f_1+f_2+f_3}{3}\right)^3 K_3(f_1,f_2,f_3) \quad (64)$$

$$\approx \frac{1}{x_2-x_1}\int_{x_1}^{x_2}\beta(x)\alpha(f,x)[\{\beta(x)-1\}(1+\ln f) - 1]dx$$

$$= \frac{-B}{4(x_2-x_1)}\left\{\ln\left[\frac{I(f_1,x_1)}{I(f_1,x_2)}\right](f_2\ln f_2 - \right.$$

$$f_3\ln f_3) + \ln\left[\frac{I(f_2,x_1)}{I(f_2,x_2)}\right](f_3\ln f_3 - f_1\ln f_1) +$$

$$\left.\ln\left[\frac{I(f_3,x_1)}{I(f_3,x_2)}\right](f_1\ln f_1 - f_2\ln f_2)\right\}\left(\frac{f_1+f_2+f_3}{3}\right)^2\left(1+\right.$$

$$\left.\ln\frac{f_1+f_2+f_3}{3}\right)^3 + L_3',$$

where

-continued $$L_3' = \frac{B}{4(x_2-x_1)}\{[a(f_1,x_2) - a(f_1,x_1)]\ln f_1(f_2\ln f_2 - f_3\ln f_3) +$$

$$[a(f_2,x_2) - a(f_2,x_1)]\ln f_2 \cdot (f_3\ln f_3 - f_1\ln f_1) +$$

$$[a(f_3,x_2) - a(f_3,x_1)]\ln f_3(f_1\ln f_1 - f_2\ln f_2)\}\left(\frac{f_1+f_2+f_3}{3}\right)^2\left(1+\right.$$

$$\left.\ln\frac{f_1+f_2+f_3}{3}\right)^3$$

$$B = \frac{2}{(f_1\ln f_1 - f_2\ln f_2)(f_2\ln f_2 - f_3\ln f_3)(f_1\ln f_1 - f_3\ln f_3)}$$

The equation which gives $\beta(x)$ and corresponds to Eq.(42) becomes as follows:

$$\beta(x) = \frac{f_1+f_2+f_3}{3}\left(1+\ln\frac{f_1+f_2+f_3}{3}\right)\cdot \quad (65)$$

$$\frac{K_3}{K_2} + \frac{2+\ln\frac{f_1+f_2+f_3}{3}}{1+\ln\frac{f_1+f_2+f_3}{3}}$$

$$= \frac{1}{1+\ln\frac{f_1+f_2+f_3}{3}}\cdot$$

$$\left[\frac{K_3'}{K_2'} + \left(2+\ln\frac{f_1+f_2+f_3}{3}\right)\right]$$

Likewise, the equation which gives $\alpha(f,x)$ and corresponds to Eq.(43) becomes as follows:

$$\alpha(f,x) = \frac{K_2}{\frac{K_3}{K_2} + \left[\left(2+\ln\frac{f_1+f_2+f_3}{3}\right)\Big/\left\{\frac{f_1+f_2+f_3}{3}\cdot\left(1+\ln\frac{f_1+f_2+f_3}{3}\right)^2\right\}\right]} \quad (66)$$

$$= \frac{K_2'\left(1+\ln\frac{f_1+f_2+f_3}{3}\right)}{\frac{K_3'}{K_2'} + \left(2+\ln\frac{f_1+f_2+f_3}{3}\right)}$$

Figure 12:
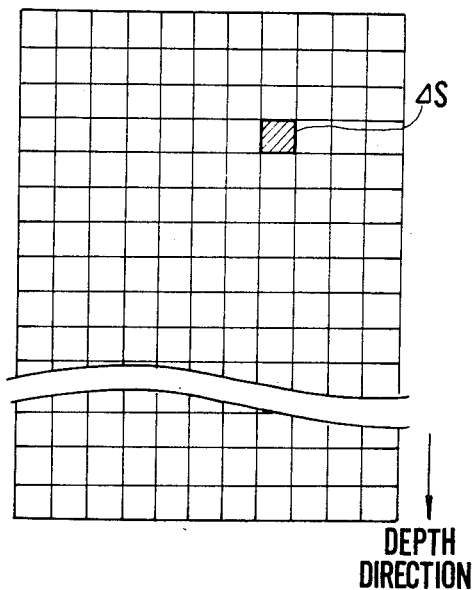
FIG. 12 is a view useful in describing another display mode of the apparatus embodied in FIG. 6.

If the coefficient $a(f,x)$ of the frequency dependence $f^{a(f,x)}$ of reflection intensity is constant within the range of frequencies measured, namely if $a(f_1,x_1)=a(f_2,x_1)=a(f_3,x_1)=a(x_1)$ and $a(f_1,x_2)=a(f_2,x_2)=a(f_3,x_2)=a(x_2)$ hold, then $a(f,x)$ will be a function solely of $x$, thus Eqs.(63) and (64) will become as follows:

$$K_2' \approx \frac{1}{x_2-x_1}\int_{x_1}^{x_2}\beta(x)\alpha\left(\frac{f_1+f_3}{2},x\right)dx \quad (67)$$

$$= \frac{f_1+f_3}{8(x_2-x_1)(f_1\ln f_1 - f_3\ln f_3)}\left(1+\right.$$

$$\left.\ln\frac{f_1+f_3}{2}\right)\ln\left[\frac{I(f_1,x_1)}{I(f_1,x_2)}\Big/\frac{I(f_3,x_1)}{I(f_3,x_2)}\right] +$$

played as an image. This becomes feasible if an algorithm similar to that described above is applied with respect to each unit pixel Δs of the image, as shown in FIG. 12.

Though the distribution image naturally has poorer spacial resolution in comparison with the B-mode image, a fundamental difference is that attenuation coefficient-related information absolutely unmeasurable with the prior art can be obtained as the displayed information.

In the illustrated embodiment, a wide-band probe is used as the probe 1. However, as described in the specification of Japanese Patent Application Laid-Open No. 56-147082, it is permissible to employ a probe having a plurality of different frequency bands. Further, to facilitate the description of the illustrated embodiment, the elements constituting the arithmetic unit 11 have been described as if they were constituted by hardware. Though hardware may of course be used, the funtions of these elements can also be implemented by the software of the CPU 400.

According to the present invention as described and illustrated above, the intensity of an echo from an object under investigation is measured at a plurality of different frequencies, whereby the attenuation coefficient of the object as well as the frequency dependence of the attenuation coefficient can be measured by approximation. It is also possible to obtain a distribution image of the values obtained. Therefore, unlike the conventional ultrasonic tomographic measurement method and apparatus with which only morphological information can be obtained, the present invention makes it possible to obtain quantitative information relating to attenuation within the object.

The subject matter of the present invention described in connection with the illustrated embodiment should be interpreted in accordance with the appended claims, and any modifications of the illustrated embodiment that may readily occur to one skilled in the art are covered by the appended claims.

What is claimed is:

1. An ultrasonic measurement method for obtaining quantitative information relating to ultrasonic characteristics of an object under investigation, comprising the steps of:
   (a) transmitting ultrasonic pulses having a plurality of different frequencies into the object under investigation,
   (b) detecting echos of the ultrasonic pulses reflected from within the object,
   (c) subjecting the detected echos, which exhibit a plurality of frequencies, to information processing to derive a mean value of attenuation coefficients measured on the basis of two different frequencies, and a mean value of attenuation coefficients measured on the basis of three different frequencies inclusive of the first two frequencies; and
   (d) deriving information relating to an attenuation coefficient of the object from said mean value of attenuation coefficients measured on the basis of two different frequencies, and said mean value of attenuation coefficients measured on the basis of three different frequencies inclusive of the first two frequencies.

2. The method according to claim 1, wherein the information relating to the attenuation coefficient includes an attenuation coefficient of ultrasonic waves within the object.

3. The method according to claim 1, wherein the information relating to the attenuation coefficient includes frequency dependence of the attenuation coefficient of ultrasonic waves within the object.

4. The method according to claim 2, wherein the information relating to the attenuation coefficient includes frequency dependence of the attenuation coefficient of ultrasonic waves within the object.

5. An ultrasonic measurement method for obtaining quantitative information relating to ultrasonic characteristics of an object under investigation, comprising the steps of:
   (a) transmitting ultrasonic pulses having a plurality of different frequencies into the object under investigation,
   (b) detecting echos of the ultrasonic pulses reflected from within the object,
   (c) subjecting the detected echos, which exhibit a plurality of frequencies, to information processing to derive a mean value of attenuation coefficients measured on the basis of two different frequencies, and a mean value of a function of both attentuation coefficients and frequencies measured on the basis of three different frequencies inclusive of the first two frequencies; and
   (d) deriving information relating to an attenuation coefficient of the object from said mean value of attenuation coefficients measured on the basis of two different frequencies and said mean value of a function of both attentuation coefficients and frequencies measured on the basis of three different frequencies inclusive of the first two frequencies.

6. The method according to claim 5, wherein the information relating to the attenuation coefficient includes an attenuation coefficient of ultrasonic waves within the object.

7. The method according to claim 5, wherein the information relating to the attenuation coefficient includes frequency dependence of the attenuation coefficient of ultrasonic waves within the object.

8. The method according to claim 6, wherein the information relating to the attenuation coefficient includes frequency dependence of the attenuation coefficient of ultrasonic waves within the object.

9. An ultrasonic measurement apparatus comprising:
   transmitting means for transmitting ultrasonic pulses having a plurality of different frequencies into an object under investigation;
   detection means for detecting echos of the ultrasonic pulses reflected from within the object;
   processing means for subjecting the detected echos, which exhibit a plurality of frequencies, to information processing to obtain quantitative information relating to ultrasonic characteristics of the object, wherein said processing means includes means for obtaining a mean value of attenuation coefficients having two different frequencies, and a mean value of attenuation coefficients having three different frequencies inclusive of the first two frequencies, and means for deriving information relating to an attenuation coefficient of the object on the basis of the mean values obtained; and
   display means for displaying said quantitative information in addition to a tomograph.

10. An ultrasonic measurement apparatus comprising:
    transmitting means for transmitting ultrasonic pulses having a plurality of different frequencies into an object under investigation;

detection means for detecting echos of the ultrasonic pulses reflected from within the object;

processing means for subject the detected echos, which exhibit a plurality of frequencies, to information processing to obtain quantitative information relating to ultrasonic characteristics of the object, wherein said processing means includes means for obtaining a mean value of attenuation coefficients measured on the basis of two different frequencies, and a value of a function of mean values of both attenuation coefficients and frequencies having three different frequencies inclusive of the first two frequencies, and means for deriving information relating to an attenuation coefficient of the object on the basis of the mean values obtained; and display means for displaying said quantitative information in addition to a tomograph.

* * * * * data, and an I/O port 403 serving as an input/output control interface between the CPU 400 and the scanning section 8, an arithmetic circuit 11 and other circuits.

The ultrasonic echo received from the interior of the living body 4 is weakened by attenuation and spread of the ultrasonic beam. The purpose of the STC circuit is to vary the gain of the receiving system timewise during each sweep to apply a correction to, e.g., attenuation ascribable to distance.

Figure 7:
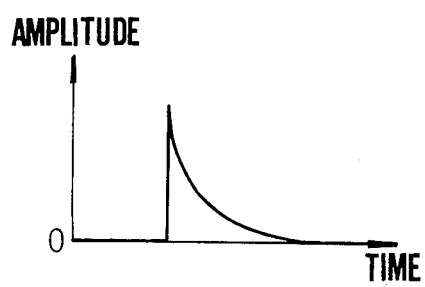
FIGS. 7 and 8 are waveform diagrams illustrating pulse waveforms useful in describing the operation of the embodiment shown in FIG. 6.
Figure 8:
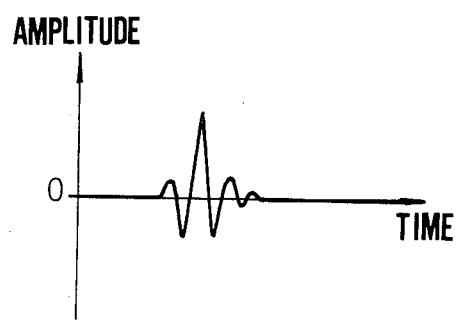

The transmitting circuit 5 supplies the probe 1 with a wide band drive pulse that undergoes sharp attenuation, as shown in FIG. 7. The probe 1 has a wide-band characteristic and preferably comprises a piezo-electric polymer [polyvinylidene fluoride (PVDF)] transducer, a composite transducer consisting of a piezo-electric polymer and inorganic matter, or a PZT transducer equipped with an acoustic matching layer. The result of using such a probe is that the probe will transmit a wide-band ultrasonic pulse of the kind shown in FIG. 8 into the interior of the object 4. It goes without saying that the frequencies $f_1$, $f_2$, $f_3$ preset for calculating $\alpha$, $\alpha_o$ and $\beta$ fall within the frequency band of this wide-band ultrasonic pulse.

An ultrasonic echo reflected or scattered at a surface (e.g., surface 2 or 3 in FIG. 1) within the object 4 having a discontinuous acoustic characteristic is received by the same probe 1 and applied thereby to the receiving circuit 7. Here the echo is converted into an amplified echo signal (A-mode signal) and then applied to an A/D converter 9 for conversion into a digital quantity stored in a memory 10. As performed in the prior art, a B-mode picture is obtained by scanning the probe 1 above the object 4 by means of the scanning section 8, and collecting the A-mode signals. Many scanning methods are available, including a mechanical sector scan, a compound scan, a linear electronic scan and a sector electronic scan. The details of these scanning methods do not have a direct bearing upon the present invention and will therefore not be described here. The echo signal obtained by such scanning enters the logarithmic amplifier 18 via the receiving circuit 7. The signal is logarithmically amplified by the amplifier 18, is detected by the detector 19 and is then subjected to an STC correction by STC circuit 20. The STC-corrected echo signal is stored in a memory 22 and is developed by a picture output amplifier circuit 14 into a B-mode picture for display on a display unit 15. The circuitry for producing the B-mode picture output is well-known and need not be described here.

If the writing (entry) of data into the memory 22 is halted and the information within the memory 22 is output repeatedly (i.e., played back), a "frozen" B-mode picture is developed for display by the display unit 15.

On the other hand, the method in which the B-mode picture can be displayed simultaneously with the scanning, is actually available in real-time ultrasound scanner apparatus using a linear electronic scan method. In this apparatus, we may utilize so-called "freezing function" to obtain desired tomograph.

Figure 6:
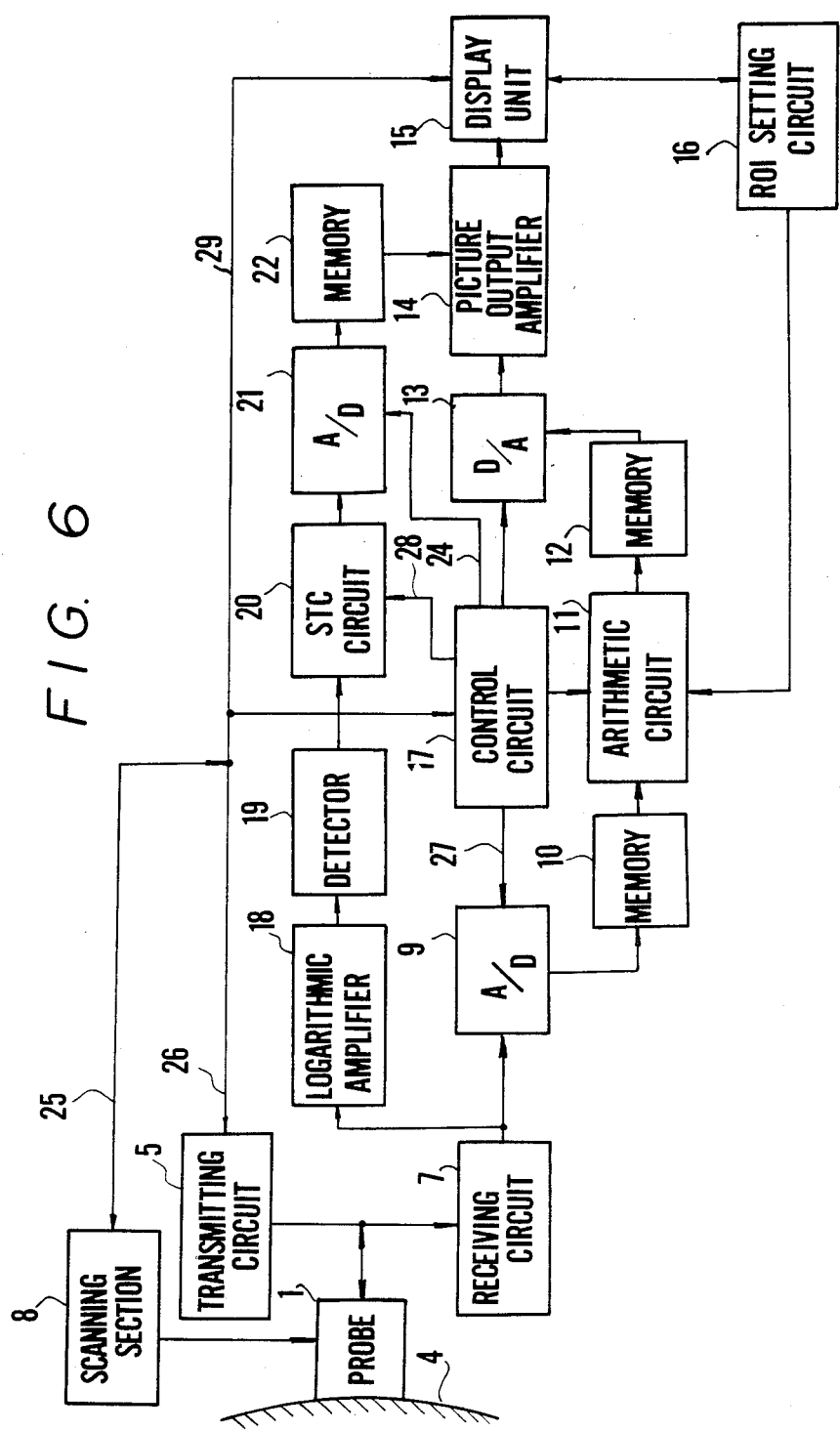
FIG. 6 is a block diagram illustrating an embodiment of an apparatus for practicing the ultrasonic measurement method of the present invention.

More particularly, an observer can make a freeze switch (not shown in FIG. 6) function so that writing the data into the memory 22 may be prohibited and the data in memory 22 may be developed to be displayed in display unit 15 as a stationary picture continuously. Writing the data into memory 22 will restart by releasing the freeze switch, thus providing a dynamic picture to be displayed in display unit 15.

Figure 10:
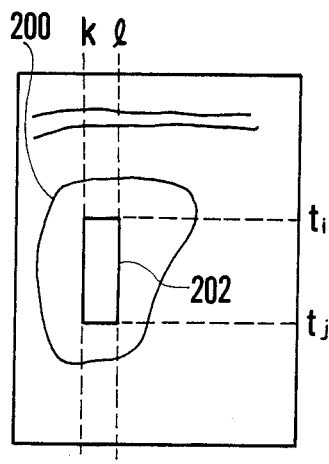
FIG. 10 is a view illustrating an example of an ultrasonic tomograph displayed by the apparatus embodied in FIG. 6.

As shown in FIG. 10, the frozen picture, indicated at 200, has a region of interest 202, in which $\alpha(f,x)$, $\alpha_o(x)$ and $\beta(x)$ are desired to be measured, designated thereon by a circuit 16 for setting the region of interest (ROI). This is performed by manipulating a control member (not shown) of the setting circuit 16 to designate the intervals of the area of interest by a frame 202, as shown in FIG. 10. This method is similar to a method of measuring the distance between two points by so-called caliper measurement.

In accordance with a predetermined algorithm shown in FIGS. 9(a) through 9(f), the A mode signal stored in the memory 10 is processed by the arithmetic circuit 11 to obtain $\beta(x)$, $\alpha_o(x)$ and $\alpha(f,x)$, the values whereof are then stored in a memory 12. The values of $\beta(x)$, $\alpha_o(x)$ and $\alpha(f,x)$ are selected from the memory 12 when required, the selected value is converted into an analog quantity by a D/A converter 13, and the resulting analog signal is applied to the picture output amplifier circuit 14 where the signal is amplified and delivered to the display unit 15 as a visible picture.

The operation of the ultrasonic measurement apparatus of the present invention will now be described with reference to the flowcharts of FIGS. 9(a) through 9(f). The operational flow is divided into two portions, namely a portion for processing up to the B-mode display and a portion for calculation of $\alpha(f,x)$, $\alpha_o(x)$ and $\beta(x)$.

The program starts with processing for the B-mode display. The CPU 400 drives the transmitting circuit 5 via a control line 26 at a step 300. As mentioned above, the probe 1 is driven by the transmitting circuit 5 and projects ultrasonic waves into the object 4, assumed here to be a living body. The CPU 400 sets the scanning section 8 into operation via a control line 25 at a step 302. The scanning section 8 responds by sending a synchronizing signal to the probe 1 and CPU 400. As a result, the sweep of the probe 1 and the operation of the scanning section 8 and CPU 400 are synchronized. At the same time that the probe 1 starts to be swept in step 302, the CPU 400 executes a step 304 to instruct the A/D converter circuits 9, 21, via control lines 27, 24, respectively, to begin an analog-to-digital conversion operation. The CPU 400 simultaneously executes a step 306, in which the STC circuit 20 is placed in operation via a control line 28 in order to perform an STC correction. It goes without saying that the operations indicated by steps 300 through 306 are performed substantially simultaneously.

Thus, one sweep of an A-mode signal for a B-mode display is stored in the memory 22, and an A-mode signal for calculating $\alpha(f,x)$, $\alpha_o(x)$ and $\beta(x)$, which is an object of the invention, is stored in the memory 10 (step 308).

The foregoing sweeping operation is performed for a full set of scanning lines. In other words, it is determined at a step 312 whether a full scan has beem completed, with steps 300 through 312 being repeated when the decision in step 312 is NO.

As previously described, when the freeze-switch functioned, the flow goes from step 312 to step 314 unconditionally. In this manner, A-mode signals for the entire scanning area are stored in the memories 10, 22. When a full scan is completed, i.e., when the answer is YES in step 312, the A-mode signals stored in the memory 22 are luminance-modulated by the picture output amplifier 14 and displayed on the display unit 15 (step 314). It should be noted that a control line 29 carries a synchronizing signal for the display unit 15.

Described next will be the arithmetic circuit 11 for calculating $\alpha(f,x)$, $\alpha_o(x)$ and $\beta(x)$, the control circuitry therefore, and the calculation algorithm.

Figure 11:
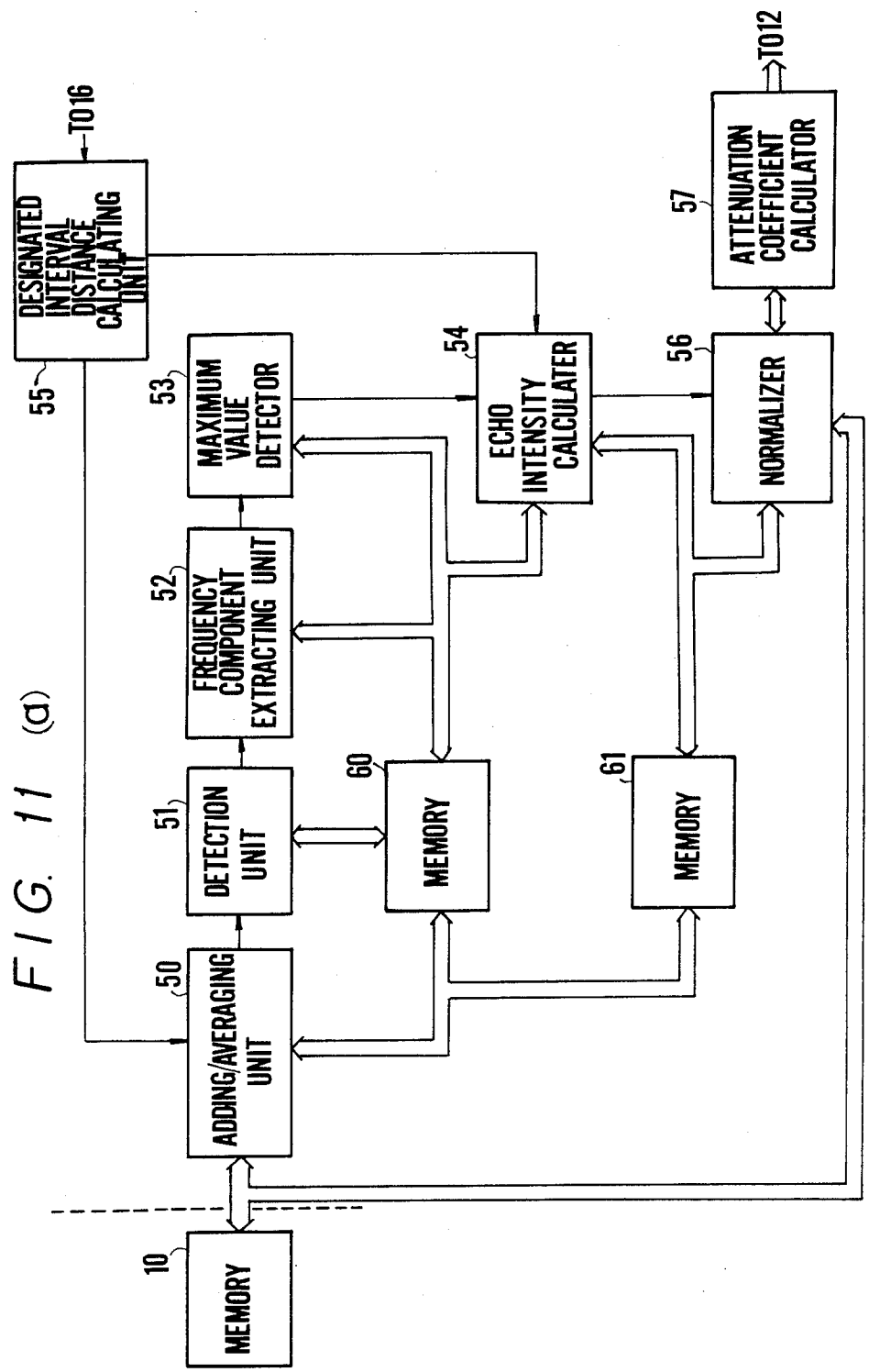
FIGS. 11(a) and (b) is a functional block diagram illustrating the functional construction of an arithmetic circuit in the apparatus embodied in FIG. 6.
Figure 11:
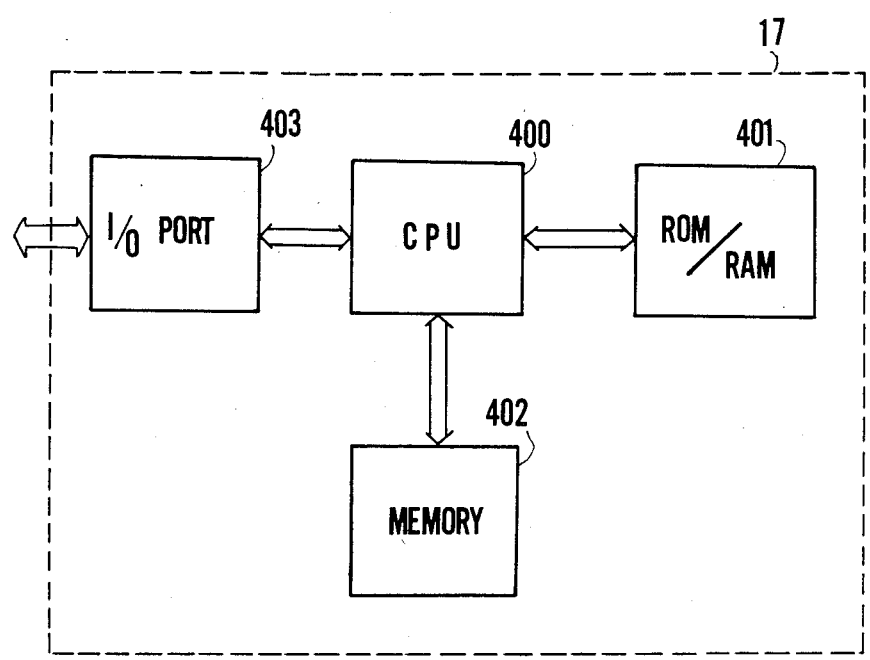

FIG. 11(a), (b) is a functional block diagram showing the arithmetic circuit 11 and a portion of the control circuit 17. Illustrated are both the CPU 400, ROM/RAM 401, memory 402, I/O port 403 of the control circuit 17 and the various components of arthmetic circuit 11. The role played by control circuit 17 is as described above. Though the details are not specifically shown in FIG. 11, the elements constituting the arithmetic circuit 11 operate under the control of the CPU 400. The flow of data in FIG. 11 is indicated by the bold arrows, while the flow of control signals is shown by the slender arrows.

The algorithm for processing executed by the arithmetic circuit 11 under the control of the CPU 400 will now be described in conjunction with the flowcharts of FIGS. 9(b) through 9(f). The flowcharts are shown on the left side of FIGS. 9(b) through 9(f), while the results of associated processing are indicated in the form of graphs or the like on the right side at positions corresponding to the relevant process steps.

As described above, the CPU 400, at the steps 300 through 314 for scanning the probe 1 to produce the B-mode display, causes the A/D converter circuit 9 to convert the echo signal from the receiving circuit 7 into a digital signal, and stores the digital signal in the memory 10. When an entire scan is completed, therefore, echo signals for an entire zone are stored in the memory 10 in digital form. Meanwhile, the display unit 15 presents a B-mode display.

Figure 5:
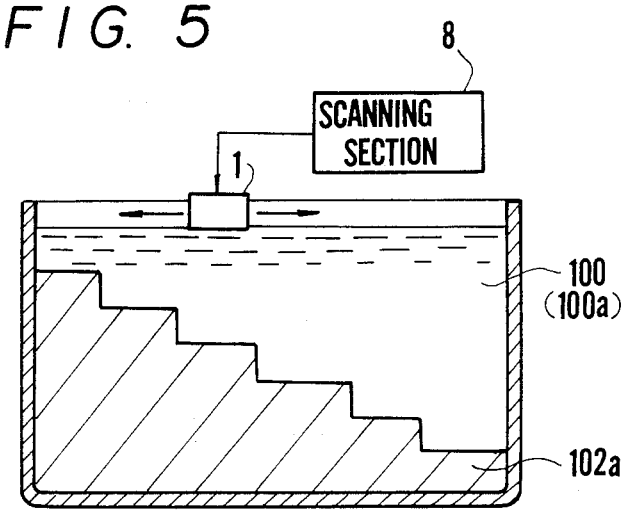

As shown at step 316, the CPU 400 applies a pixel address of an area designated by the region of interest setting circuit 16 to a designated interval distance calculating unit 55 as a scanning line interval and time interval, as shown in FIG. 10. In other words, scanning lines k, l and arrival times $t_i$, $t_j$ of the ultrasonic waves are stored in the calculating unit 55. The program moves to step 318, where a standard sound pressure curve $J(f,x)$ in the memory 402 of the CPU 400 is stored in a portion of the memory 10. As mentioned above, the standard sound pressure curve $J(f,x)$ stored in the memory 402 may be remeasured through the method shown in FIG. 5 to update the contents of the memory.

Next, the CPU sets an adding and averaging unit 50 into operation at a step 320. The adding and averaging unit 50 then reads, out of the memory 10, the A-mode signals in the interval designated by the values of k, l, $t_i$, $t_j$ stored in the designated interval distance calculating unit 55, adds and computes the mean of these signals, produces a signal 1000 indicative of the result and stores the signal in a memory 60 at a step 322. For the purpose of latter processing, the A-mode signal 1000 stored in the memory 60 is also stored in a memory 61 at a step 324.

The CPU 400 then starts a detection unit 51 at a step 326. The detection unit 51 responds by subjecting the A-mode signal stored in the memory 60 to detection processing. An A-mode signal 1001 resulting from the detection processing is stored in the memory 60 at a step 328. Next, the CPU starts a high-frequency component extracting unit 52 at a step 330. The extracting unit 52 sends the detected A-mode signal 1001 through a high-pass filter to produce an A-mode signal 1002 from which the low frequency component has been removed (step 332). Then, at a step 334, a portion of the A-mode signal 1002 below a predetermined level ($L_o$) is cut off to remove noise, thereby resulting in an A-mode signal 1003 which is to be stored in the memory 60.

Figure 9:
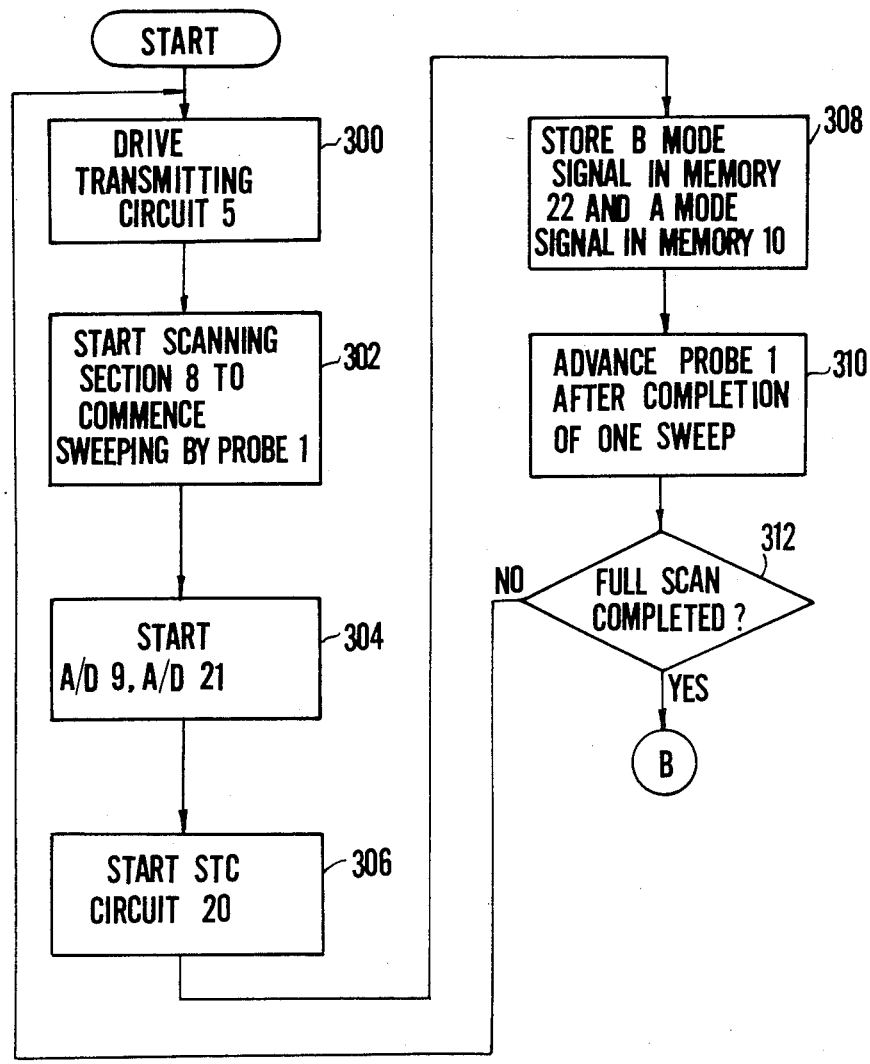
FIGS. 9(a) through 9(f) are flowcharts illustrating the operating steps of the apparatus embodied in FIG. 6.
Figure 9:
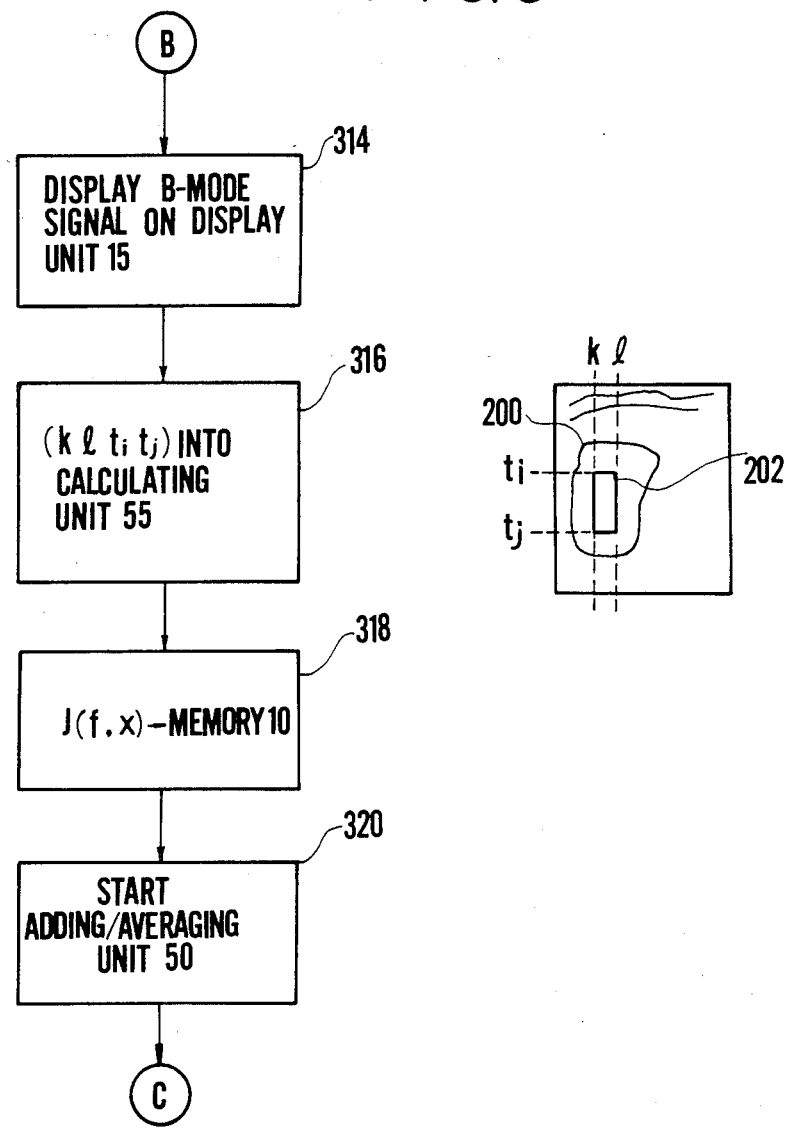
Figure 9C:
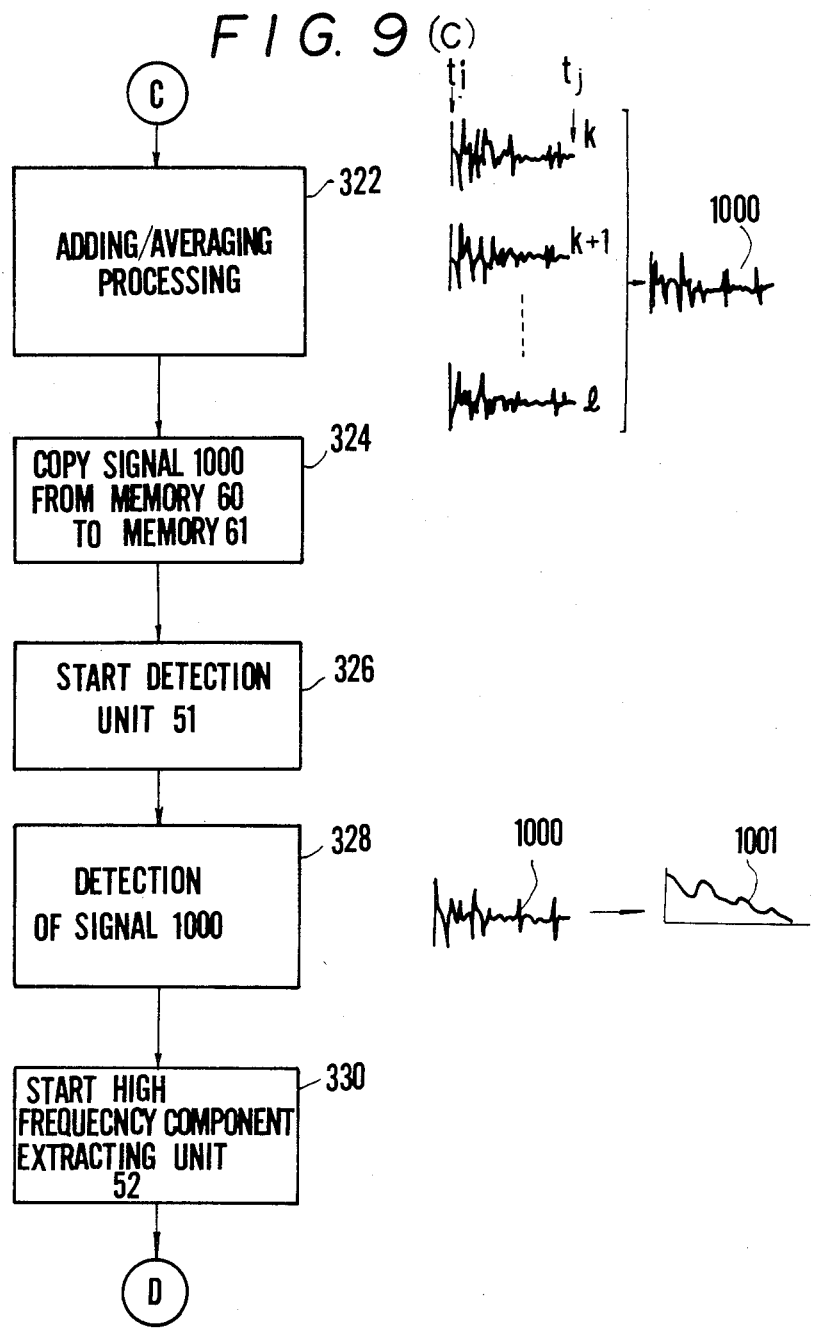
Figure 9:
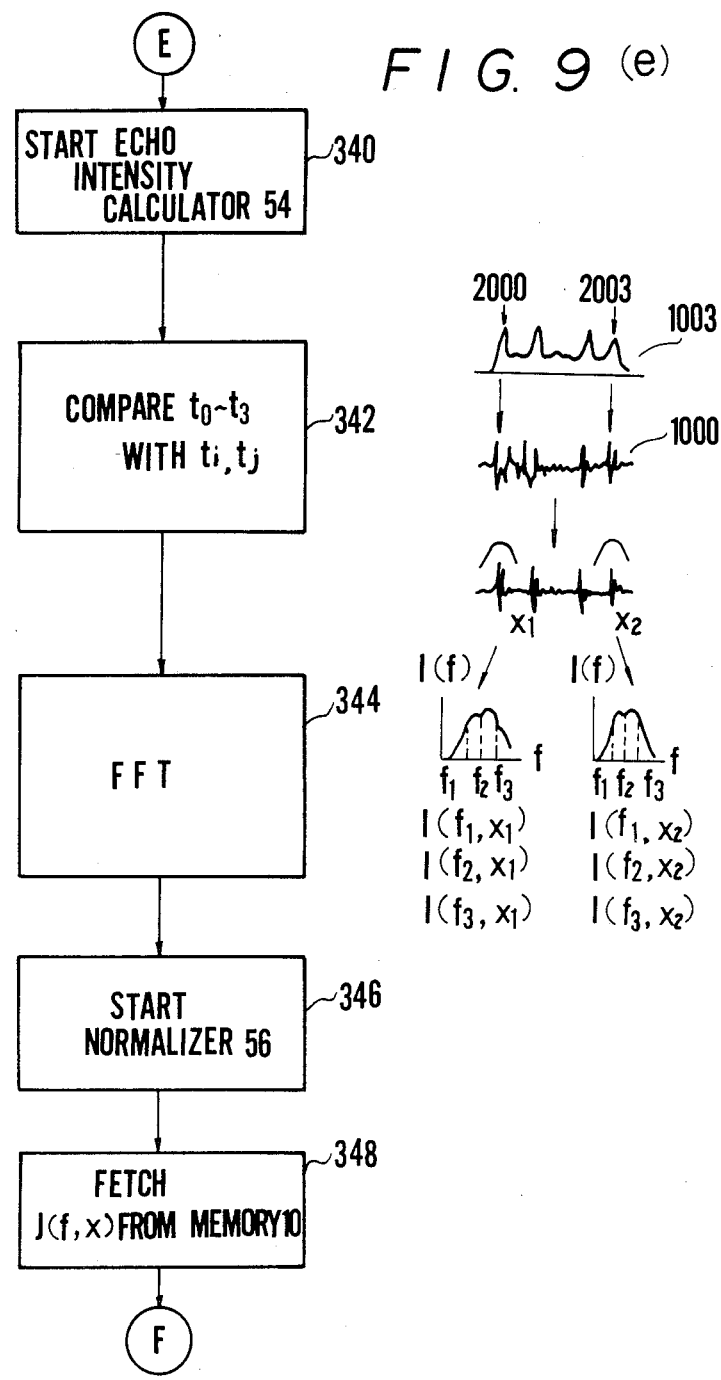

Next, the CPU 400 starts a maximum value detecting unit 53 at a step 336, the unit 53 responding by detecting the position (time) of the maximum value of the A-mode signal 1003. The maximum values detected are 2000, 2001, 2002 and 2003 (step 338). Thus, in the present case, the designated interval contains four points at which the acoustic characteristic is discontinuous. These points appear at times (positions) $t_o$, $t_1$, $t_2$, $t_3$. These values are stored into memory 60. The CPU 400 then starts an echo intensity calculating unit 54 at a step 340. The echo intensity calculating unit 54 is adapted to find the maximum and minimum values from among the values at $t_o$, $t_1$, $t_2$, $t_3$ in the time interval $t_i - t_j$ stored in the designated interval distance calculating unit 55. In the example of FIG. 9(e), these values are located at $t_o$ and $t_3$ (step 342). Next, a Hamming window of a predetermined width is applied with regard to the A-mode signal corresponding to $t_o$ and $t_3$, a fast Fourier transform is performed to obtain $I(f)$, and $I(f_1,x_1)$, $I(f_2,x_1)$, $I(f_3,x_1)$, $I(f_1,x_2)$, $I(f_2,x_2)$, $I(f_3,x_2)$ corresponding to $f_1$, $f_2$, $f_3$ are found (step 344).

Next, the CPU 400 places a normalizing unit 56 into operation at a step 346. In order to calibrate the sound field characteristic, the normalizing unit 56 divides $I(f,x)$, obtained in step 344, by the referential value $J(f,x)$ stored in the memory 10, thus to obtain $\hat{I}(f,x)$ (steps 348, 350).

The program then moves to a step 352, where the CPU starts an attenuation coefficient calculating unit 57. At step 354, using $X_1 = C_0 t_0$, $x_2 = C_0 t_3$ (where $C_0 = 1530$ m/s is a mean value of propagation velocity in living body), the calculating unit 57 calculates the mean value $H_2$ or $K_2'$ on the basis of Eqs. (28') or (73') according to the frequency dependence of the coefficient $a(f,x)$.

At step 356, the calculating unit 57 calculates the value $H_3$ or $K_3'$ on the basis of Eqs. (29) or (74). From the values of both $H_2$ or $K_2'$ and $H_3$ or $K_3'$, the calculating unit 57 calculates $\beta(x)$, $\alpha(f,x)$, according to Eqs. (32), (33) or (75), (76) at step 360, thus providing $\alpha_0(x)$ from the equation $\alpha_o(x) = \alpha(f,x)/f^{\beta(x)}$ at step 362. As described above, we substitute $\hat{I}(f,x)$ for $I(f,x)$ in the equations appearing at stop 354 through 356.

Next, at a step 364, the calculated values of $H_2$, $H_3$, $\beta(x)$, $\alpha(f,x)$ and $\alpha_o(x)$ are stored in the memory 12. Thus, the sought values of $\alpha$, $\beta$, and $\alpha_o$ are obtained. In steps 368, 370, the values of either $H_2$, $H_3$, or $K_2'$, $K_3'$ in addition to $\beta(x)$, $\alpha(f,x)$ and $\alpha_o(x)$ stored in the memory 12 are delivered to the display unit 15 through the picture output amplifier 14. These values are displayed by the display unit 15 together with the B-mode picture read out of the memory 21.

Though $\alpha(f,x)$ is expressed in Neper/cm units, a conversion into dB/cm units can be made within the arithmetic circuit 11 if necessary. Alternatively, it is also possible to display $\beta(x)$. In addition, $\alpha_o(x)$ can be displayed in dB/cm MHz units.

It should be noted that with a second display mode presented by the inventive apparatus, rather than measuring the attenuation coefficient solely within the designated interval, $H_2$, $H_3$, $K_2'$, $K_3'$, $\beta(x)$, $\alpha_o(x)$ and $\alpha(f,x)$ per unit pixel (interval) with respect to the entire picture can be measured and the distribution thereof dis-

UNITED STATES PATENT AND TRADEMARK OFFICE
CERTIFICATE OF CORRECTION

PATENT NO. : 4,566,330
DATED : January 28, 1986
INVENTOR(S) : Tadashi FUJII et al It is certified that error appears in the above-identified patent and that said Letters Patent is hereby corrected as shown below:

IN THE ABSTRACT:

lines 3 and 4, change "are transmitted into in order to object under investigation and derive" to --are transmitting into an object under investigation in order to derive--.

Signed and Sealed this

Second Day of September 1986

[SEAL]

Attest:

DONALD J. QUIGG

Attesting Officer     Commissioner of Patents and Trademarks

UNITED STATES PATENT AND TRADEMARK OFFICE
CERTIFICATE OF CORRECTION

PATENT NO. :     4,566,330
DATED      :     January 28, 1986
INVENTOR(S) :    Tadashi FUJII et al It is certified that error appears in the above-identified patent and that said Letters Patent is hereby corrected as shown below:

IN THE ABSTRACT:

lines 3 and 4, change "are transmitted into in order to object under investigation and derive" to --are transmitting into an object under investigation in order to derive--.

Signed and Sealed this

Second Day of September 1986

[SEAL]

Attest:

DONALD J. QUIGG

Attesting Officer

Commissioner of Patents and Trademarks